United States Patent
Lenting et al.

(10) Patent No.: US 10,544,231 B2
(45) Date of Patent: Jan. 28, 2020

(54) ANTIBODIES FOR THE PREVENTION OR THE TREATMENT OF BLEEDING EPISODES

(71) Applicants: INSERM (Institut National de la Santé et de la Recherche Médicale), Paris (FR); UNIVERSITE PARIS—SUD, Orsay (FR); CENTRE HOSPITALIER REGIONAL UNIVERSITAIRE DE LILLE, Lille (FR); UNIVERSITÉ DE DROIT ET DE LA SANTÉ DE LILLE 2, Lille (FR)

(72) Inventors: Petrus Lenting, Le Kremlin-Bicetre (FR); Cécile Denis, Le Kremlin-Bicetre (FR); Olivier Christophe, Le Kremlin-Bicetre (FR); Paulette Legendre, Le Kremlin-Bicetre (FR); Antoine Rauch, Lille (FR); Sophie Susen, Lille (FR)

(73) Assignees: INSERM (Institut National de la Santé et de la Recherche Médicale), Paris (FR); UNIVERSITE PARIS—SUD, Orsay (FR); CENTRE HOSPITALIER REGIONAL UNIVERSITAIRE DE LILLE, Lille (FR); UNIVERSITÉ DE DROIT ET DE LA SANTÉ DE LILLE 2, Lille (FR)

( * ) Notice: Subject to any disclaimer, the term of this patent is extended or adjusted under 35 U.S.C. 154(b) by 434 days.

(21) Appl. No.: 15/303,889

(22) PCT Filed: Apr. 16, 2015

(86) PCT No.: PCT/EP2015/058313
§ 371 (c)(1),
(2) Date: Oct. 13, 2016

(87) PCT Pub. No.: WO2015/158851
PCT Pub. Date: Oct. 22, 2015

(65) Prior Publication Data
US 2017/0037148 A1 Feb. 9, 2017

(30) Foreign Application Priority Data
Apr. 16, 2014 (EP) .................................. 14305569

(51) Int. Cl.
*C07K 16/36* (2006.01)
*A61K 39/395* (2006.01)

(52) U.S. Cl.
CPC .......... *C07K 16/36* (2013.01); *C07K 2317/24* (2013.01); *C07K 2317/34* (2013.01); *C07K 2317/565* (2013.01); *C07K 2317/70* (2013.01); *C07K 2317/92* (2013.01)

(58) Field of Classification Search
None
See application file for complete search history.

(56) References Cited

U.S. PATENT DOCUMENTS 6,228,360 B1 * 5/2001 Co ........................ C07K 16/36
424/145.1

FOREIGN PATENT DOCUMENTS

| WO | WO-9515982 A2 * | 6/1995 | ............. C07K 16/00 |
| WO | WO-2005108430 A2 * | 11/2005 | ......... C07K 16/3084 |
| WO | 2012/006591 A1 | 1/2012 | |
| WO | WO-2015116753 A1 * | 8/2015 | ......... C07K 16/3092 |

OTHER PUBLICATIONS

Zanardelli et al., Blood. Sep. 24, 2009;114(13):2819-28. doi: 10.1182/blood-2009-05-224915. Epub Jul. 8, 2009.*
Janeway et al., Immunobiology, 3rd edition, 1997, Garland Publishing Inc., pp. 3:1-3:11.*
Rudikoff et al., Proc Natl Acad Sci U S A. Mar. 1982;79(6):1979-83.*
Romijn et al., J Biol Chem. Mar. 30, 2001;276(13):9985-91. Epub Nov. 29, 2000.*
Kipryanov et al., Mol Biotechnol. Jan. 2004;26(1):39-60.*
Meyer et al., Br J Haematol. Aug. 1984;57(4):597-608.*
Meyer et al., Br J Haematol. Aug. 1984;57(4):609-620.*

(Continued)

*Primary Examiner* — Michael Szperka
(74) *Attorney, Agent, or Firm* — W&C IP

(57) ABSTRACT

The invention relates to an isolated monoclonal antibody that specifically binds to the D4 domain of VWF, competes for binding to VWF D4 domain with ADAMTS13 and partially inhibits ADAMTS 13-mediated degradation of VWF. More particularly, the invention relates to an isolated monoclonal antibody comprising a heavy chain wherein the variable domain comprises at least one CDR having a sequence selected from the group consisting of SEQ ID NO: 3 for H-CDR1, SEQ ID NO: 4 for H-CDR2 and SEQ ID NO: 5 for H-CDR3 and a light chain wherein the variable domain comprises at least one CDR having a sequence selected from the group consisting of SEQ ID NO: 7 for L-CDR1, SEQ ID NO: 8 for L-CDR2 and SEQ ID NO: 9 for L-CDR3. Antibodies of the invention are presented to be useful in for the prevention or the treatment of bleeding episodes, such as bleeding episodes occurring in patients with aortic stenosis or patients with ventricular assist devices (VAD).

Figure 1:
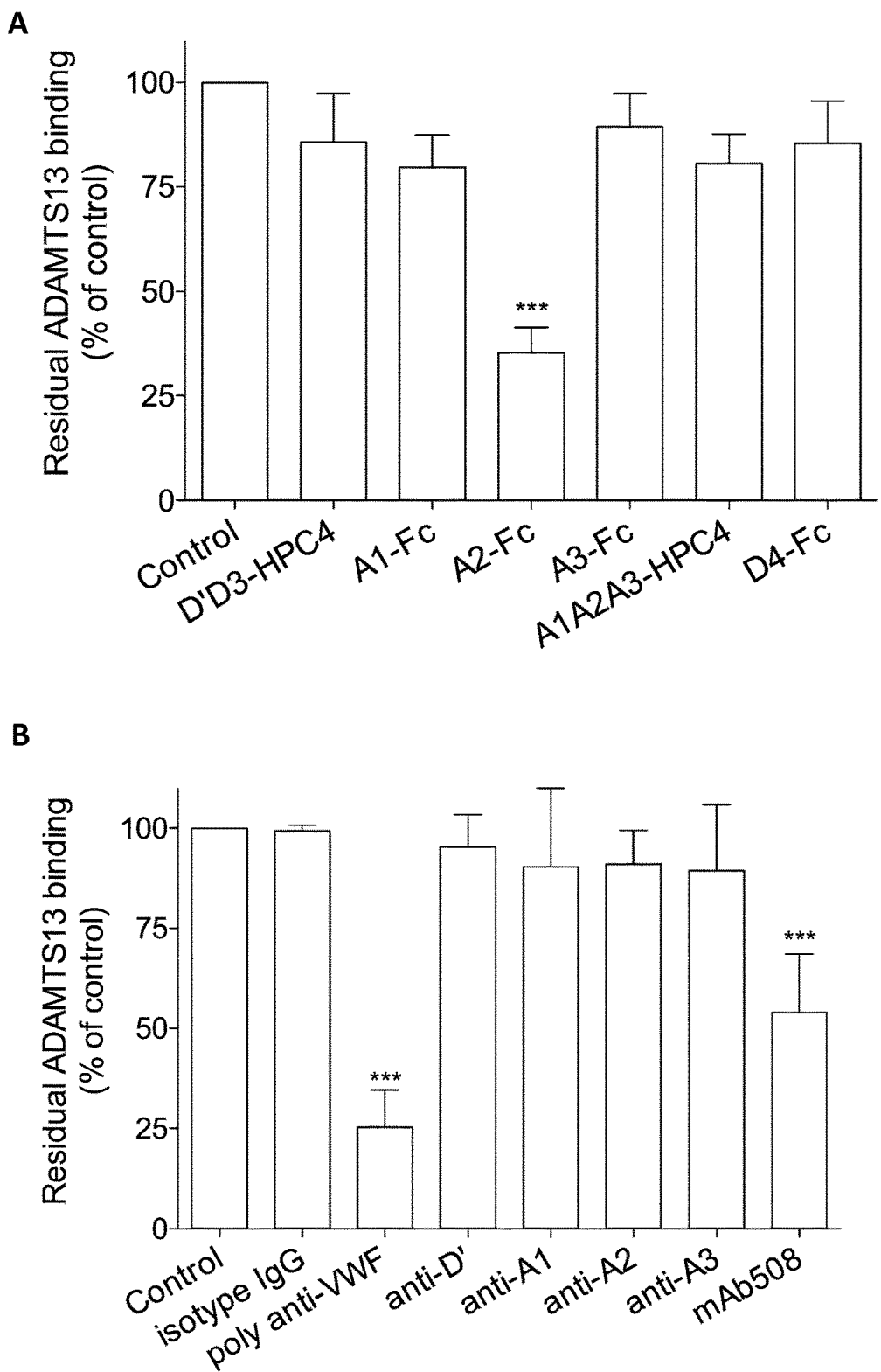

11 Claims, 5 Drawing Sheets
Specification includes a Sequence Listing.

(56) References Cited

OTHER PUBLICATIONS

Rauch et al., Thromb Haemost. Nov. 2014;112(5):1014-23. doi: 10.1160/TH14-02-0148. Epub Jul. 17, 2014.*
S. Zanardelli et al: "A novel binding site for ADAMTS13 constitutively exposed on the surface of globular VWF", Blood, vol. 114, No. 13, Jul. 8, 2009, pp. 2819-2828.
Marcus Stokschlaeder et al: "Update on von Willebrand factor multimers", Blood Caogualtion & Fibronolysis, vol. 25, No. 3, Apr. 1, 2014, pp. 206-216.
M. Furlan et al: "Triplet structure of von Willebrand factor reflects proteolytic degradation of high molecular weight multimers.", Proceedings of the Antional Academy of Sciences, vol. 90, No. 16, Aug. 15, 1993, pp. 7503-7507.
J. T. B. Crawley et al: "Unraveling the scissile bond: how ADAMTS13 recognizes and cleaves von Willebrand factor", Blood, vol. 118, No. 12, Jun. 29, 2011, pp. 3212-3221.
H. B. Feys et al: "Multi-step binding of ADAMTS-13 to von Willebrand factor", Journal of Thrombosis and Haemostasis, vol. 7, No. 12, Dec. 1, 2009, pp. 2088-2095.
Christopher J Lynch et al: "Control of VW A2 domain stability and ADAMTS13 access to the scissile bond of full-length VWF", Jan. 20, 2014.

* cited by examiner

ANTIBODIES FOR THE PREVENTION OR THE TREATMENT OF BLEEDING EPISODES

FIELD OF THE INVENTION

The invention is in the field of immunotherapy. The invention thus relates to antibodies useful for the prevention or the treatment of bleeding episodes, especially bleeding episodes associated with acquired Von Willebrand syndrome (aVWS), such as bleeding episodes occurring in patients with aortic stenosis or patients with ventricular assist devices (VAD).

BACKGROUND OF THE INVENTION

Von Willebrand factor (VWF) is a multimeric glycoprotein that plays an essential role in the formation of platelet-rich thrombi, particularly under conditions of high shear stress. The main source of circulating VWF are the endothelial cells, where it is synthesized as a single chain pro-subunit with a discrete domain architecture, which was recently re-annotated: D1-D2-D'-D3-A1-A2-A3-D4-C1-C2-C3-C4-C5-C6-CK (1). Intra-cellular processing results in the removal of the propeptide (D1-D2 domains), and multimerization of the protein via amino- and carboxy-terminal disulfide bonding (2). These processes generate a heterologous pool of differentially sized multimers that may contain as many as 60 subunits, which are stored in the endothelial Weibel-Palade bodies and secreted into plasma via constitutive and agonist-induced pathways (3).

The multimer size of VWF is pertinent to its platelet-recruiting function, with the larger multimers displaying the highest hemostatic potential. In normal plasma, the multimers may contain between 2 and 40 subunits (1-20 bands when analyzed by SDS-agarose electrophoresis; (4)), which are shorter than those found in the endothelial storage organelles. Indeed, mechanisms are in place regulating VWF multimer size in the circulation, including proteolysis by the VWF-cleaving protease ADAMTS13 (A Disintegrin And Metalloprotease with ThromboSpondin domains-13) (5).

The molecular basis of VWF proteolysis by ADAMTS13 has been extensively studied (6). A number of interactive sites have been identified, including the A2- and D4-domains of VWF, which are important for the proper alignment of the ADAMTS13 active site (7-9). This active site attacks the Tyr1605-Met1606 peptide bond that is located within the VWF A2 domain (10). Interestingly, access to this peptide bond relies on the shear stress-induced unfolding of the substrate (for review see (11)), thereby protecting it against degradation while circulating normally, and limiting proteolysis to specific conditions. One of these conditions occurs when multiple VWF multimers assemble into large stretched bundles attached to the endothelial surface upon agonist-induced secretion. These bundles are not only capable of catching platelets, but their stretched conformation allows proteolysis by ADAMTS13 thereby preventing the release of platelet-binding ultra-large VWF multimers into the circulation (12, 13). Another condition favoring proteolysis occurs when VWF binds to platelets within the growing thrombus. This opens the ADAMTS13 cleavage site, and subsequent proteolysis results in reduction of VWF multimer size (14). Consequently, the platelet-binding capacity is diminished, avoiding excessive thrombus growth that could occlude the vessel.

The physiological relevance of ADAMTS13-mediated proteolysis of VWF is apparent from the severe thrombotic micro-angiopathy that is associated with the functional deficiency of ADAMTS13, a disorder known as thrombotic thrombocytopenic purpura (TTP) (15). In contrast, increased proteolysis of VWF by ADAMTS13 leads to a bleeding diathesis, as is exemplified by von Willebrand disease (VWD)-type 2A. VWD-type 2A is caused by mutations (mostly in the VWF A2 domain) that result in excessive proteolysis of the VWF by ADAMTS13, with a concomitant loss of the higher hemostatically active multimers (16). Another example relates to acquired von Willebrand syndrome (aVWS), where increased VWF proteolysis has been associated with various clinical settings, like aortic stenosis (17, 18) and ventricular assist devices (VADs) therapy (19, 20). Both conditions are characterized by an increased incidence of bleedings, especially gastrointestinal (GI) bleedings (20, 21), in association with a selective loss of high molecular weight (HMW)-multimers and an increase in VWF degradation products (18, 22). aVWS usually resolves after aortic valve replacement or discontinuation of VAD support (18, 20, 23, 24). However, the latter is limited by graft availability and GI bleeding represents thus the most challenging complication under VAD support.

Overall there is a clear unmet medical need for a treatment targeting specifically excessive degradation of HMW-VWF multimers, for instance induced by circulatory assist devices. Ideally, such treatment should only partially interfere with VWF degradation in order to prevent drug-induced TTP-like symptoms.

SUMMARY OF THE INVENTION

In a first aspect, the invention relates to an isolated monoclonal antibody that specifically binds to the D4 domain of human von Willebrand factor (VWF), competes for binding to VWF D4 domain with A Disintegrin And Metalloprotease with ThromboSpondin domains-13 (ADAMTS13) and partially inhibits ADAMTS13-mediated degradation of VWF.

In a second aspect, the invention relates to an antibody of the invention, for use in a method for preventing or treating bleeding episodes in a patient in need thereof.

In a third aspect, the invention relates to a pharmaceutical composition comprising an antibody of the invention.

DETAILED DESCRIPTION OF THE INVENTION

The inventors hypothesized that interfering with VWF-ADAMTS13 binding exosites might subsequently provide a partial inhibition of VWF proteolysis. They identified a monoclonal anti-VWF D4 domain antibody supporting this proof of concept. Biochemical analysis revealed a potent partial inhibitory effect on VWF-ADAMTS13 interactions. Its potential to diminish VWF proteolysis was confirmed using a recently developed ex vivo model of increased VWF degradation in whole blood induced by a circulatory assist device, which faithfully reproduces the biological phenotype of aVWS.

Accordingly, the inventors showed that the antibody of the invention (mAb508) shares it specificity for the D4 domain with antibody RU8, which was recently reported to interfere with ADAMTS13-mediated degradation of VWF in a vortex-based degradation assay (8). However, degradation of HMW-multimers was fully repressed in the presence of 25 µg/ml of antibody RU8, whereas residual VWF proteolysis was still detectable at mAb508 concentrations of 45 µg/ml, indicating fundamental differences in their mode of action. The inability of mAb508 to fully inhibit VWF proteolysis, even in the presence of a vast molar excess, not only fits the requirement for partial inhibition in order to avoid TTP-like symptoms, but also allows for a wide therapeutic window.

Definitions

Throughout the specification, several terms are employed and are defined in the following paragraphs.

The term "VWF" has its general meaning in the art and refers to the human von Willebrand factor (VWF) which is a blood glycoprotein involved in blood clotting. VWF is a monomer composed of several homologous domains each covering different functions: D1-D2-D'-D3-A1-A2-A3-D4-C1-C2-C3-C4-C5-C6-CK. The naturally occurring human VWF protein has an aminoacid sequence as shown in GeneBank Accession number NP 000543.2. Monomers are subsequently arranged into dimers or multimers by cross-linking of cysteine residues via disulfide bonds. Multimers of VWF can thus be extremely large and can consist of over 40 monomers also called high molecular weight (HMW)-multimers of VWF.

The term "ADAMTS13" has its general meaning in the art and refers to the A Disintegrin And Metalloprotease with ThromboSpondin domains-13 (ADAMTS13) also known as von Willebrand factor-cleaving protease. ADAMTS13 is a zinc-containing metalloprotease enzyme that cleaves VWF. It is secreted in blood and degrades large VWF multimers, decreasing their activity. The naturally occurring human ADAMTS13protein has an aminoacid sequence as shown in GeneBank Accession number NP_620594.1

The term "anti-VWF antibody" refers to an antibody directed against VWF.

According to the invention, "antibody" or "immunoglobulin" have the same meaning, and will be used equally in the invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

The term "chimeric antibody" refers to an antibody which comprises a VH domain and a VL domain of an antibody, and a CH domain and a CL domain of a human antibody.

According to the invention, the term "humanized antibody" refers to an antibody having variable region framework and constant regions from a human antibody but retains the CDRs of a previous non human antibody.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

By "purified" and "isolated" it is meant, when referring to an antibody according to the invention or to a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

By "partial inhibition" of ADAMTS13-mediated degradation of VWF, it is meant that the degradation of high molecular weight (HMW)-multimers of VWF is not fully repressed (i.e. a significant inhibition between 50% and 80% of degradation of HMW-multimers is observed when the antibodies of the invention are used). Therefore, such partial inhibition decreases the risk of side effects provoked by a fully ADAMTS13-mediated degradation of VWF such as thrombotic thrombocytopenic purpura (TTP-like) symptoms or complications. It results that such partial inhibition may permit the use of the antibodies of the invention such as mAb508 for prevention or treatment of conditions where the reduction of ADAMTS13-mediated degradation of VWF is desirable, in particular in conditions characterised by loss of HMW-multimers of VWF caused by increased shear stress such as in patients with aortic stenosis or patients with ventricular assist devices (VAD). Such partial inhibition of degradation of HMW-multimers of an antibody of interest may be determined by an ex vivo perfusion model as described in the Example by using 45 µg/ml of said antibody.

Antibodies of the Invention:

In a first aspect, the inventions relates to an isolated monoclonal antibody that specifically binds to the D4 domain of human von Willebrand factor (VWF), competes for binding to VWF D4 domain with A Disintegrin And Metalloprotease with ThromboSpondin domains-13 (ADAMTS13) and partially inhibits ADAMTS13-mediated degradation of VWF.

In one embodiment, said antibody specifically binds to the peptide of SEQ ID NO: 1 derived from VWF D4 domain (peptide ranging from amino acids 2158-2169 of VWF) as follows: TFYAICQQDSCH The inventors have also cloned and characterized the variable domain of the light and heavy chains of said mAb508, and thus determined the complementarity determining regions (CDRs) of said antibody (Table A):

TABLE A

Sequences of mAb508 domains.

| mAb508 domains | Sequences |
| --- | --- |
| VH | SEQ ID NO: 2<br>MRVLILLCLFTAFPGLLSDVQLQESGPDLVEPSQSLSLSCT<br>VTGYSITSGYSWHWIRQFPGNKLEWLGYIHYSGTTTYNPSL<br>HSRVSITRDTSKNQFFLQLNSVSTEDTATYFCGREGYHWGQ<br>GTTLTVSSAKTTPPSVYPLAPGSAAQTNSMVTLGCLVKGYF<br>PEPVTVTWNSGSLSSGVHTFPAVLQSDLYTLSSSVTVPSST<br>WPSETVTCNVAHPASSTKVDKKIVPRDCGCKPCICTVPEVS<br>SVFIFPPKPKDVLTITLTPKVTCVVVDISKDDPEVQFSWFV<br>DDVEVHTAQTQPREEQFNSTFRSVSELPIMHQDWLNGKEFK<br>CRVNSAAFPAPIEKTISKTKGRPKAPQVYTIPPPKEQMAKD<br>KVSLTCMITDFFPEDITVEWQWNGQPAENYKNTQPIMDTDG<br>SYFVYSKLNVQKSNWEAGNTFTCSVLHEGLHNHHTEKSLSH<br>SPGK |
| H-CDR1 | SEQ ID NO: 3<br>GYSITSGYSWH |
| H-CDR2 | SEQ ID NO: 4<br>YIHYSGTTTYNPSLHS |
| H-CDR3 | SEQ ID NO: 5<br>EGYH |

TABLE A-continued

Sequences of mAb508 domains.

| mAb508 domains | Sequences |
| --- | --- |
| VL | SEQ ID NO: 6<br>MKLPVRLLVLMFWIPGSTSDVVMTQTPLSLPVSLGDQASIS<br>CRSSQSLVHSIGNTYLHWYLQKPGQSPKLLIYKVSNRFSGV<br>PDRFSGSGSGTDFTLKISRVEAEDLGVYFCSQTTHVPLTFG<br>GGTRLEIKRADAAPTVSIFPPSSEQLTSGGASVVCFLNNFY<br>PKDINVKWKIDGSERQNGVLNSWTDQDSKDSTYSMSSTLTL<br>TKDEYERHNSYTCEATHKTSTSPIVKSFNRNEC |
| L-CDR1 | SEQ ID NO: 7<br>RSSQSLVHSIGNTYLH |
| L-CDR2 | SEQ ID NO: 8<br>KVSNRFS |
| L-CDR3 | SEQ ID NO: 9<br>SQTTHVPLT |

Accordingly, in a particular embodiment, the invention relates to an isolated monoclonal antibody comprising a heavy chain, wherein the variable domain comprises at least one CDR having a sequence selected from the group consisting of SEQ ID NO: 3 for H-CDR1, SEQ ID NO: 4 for H-CDR2 and SEQ ID NO: 5 for H-CDR3.

In another particular embodiment, the invention relates an isolated monoclonal antibody comprising a light chain, wherein the variable domain comprises at least one CDR having a sequence selected from the group consisting of SEQ ID NO: 7 for L-CDR1, SEQ ID NO: 8 for L-CDR2 and SEQ ID NO: 9 for L-CDR3.

The monoclonal antibody of the invention may comprise a heavy chain wherein the variable domain comprises at least one CDR having a sequence selected from the group consisting of SEQ ID NO: 3 for H-CDR1, SEQ ID NO: 4 for H-CDR2 and SEQ ID NO: 5 for H-CDR3 and a light chain wherein the variable domain comprises at least one CDR having a sequence selected from the group consisting of SEQ ID NO: 7 for L-CDR1, SEQ ID NO: 8 for L-CDR2 and SEQ ID NO: 9 for L-CDR3.

In particular, the invention provides an monoclonal antibody comprising an heavy chain variable region comprising SEQ ID NO: 3 in the H-CDR1 region, SEQ ID NO: 4 in the H-CDR2 region and SEQ ID NO: 5 in the H-CDR3 region; and a light chain variable region comprising SEQ ID NO: 7 in the L-CDR1 region, SEQ ID NO: 8 in the L-CDR2 region and SEQ ID NO: 9 in the L-CDR3 region.

In a particular embodiment, the heavy chain variable region of said antibody has the amino acid sequence set forth as SEQ ID NO: 2 and/or the light chain variable region has the amino acid sequence set forth as SEQ ID NO: 6.

In another embodiment, the monoclonal antibody of the invention is a chimeric antibody, preferably a chimeric mouse/human antibody. In particular, said mouse/human chimeric antibody may comprise the variable domains of mAb508 antibody as defined above.

In another embodiment, the monoclonal of the invention is a humanized antibody. In particular, in said humanized antibody, the variable domain comprises human acceptor frameworks regions, and optionally human constant domain where present, and non-human donor CDRs, such as mouse CDRs as defined above.

The invention further provides fragments of said antibodies which include but are not limited to Fv, Fab, F(ab')2, Fab', dsFv, scFv, sc(Fv)2 and diabodies.

In another aspect, the invention relates to a polypeptide which has a sequence selected from the group consisting of SEQ ID NO: 1, SEQ ID NO: 2, SEQ ID NO: 3, SEQ ID NO: 4, SEQ ID NO: 5; SEQ ID NO: 6; SEQ ID NO: 7, SEQ ID NO: 8 and SEQ ID NO: 9.

In another embodiment, the invention provides s a monoclonal antibody that competes for binding to VWF D4 domain with the mAb508 as defined above.

Competitive Binding Assays:

The invention thus relates to an isolated monoclonal antibody that specifically binds to the D4 domain of human VWF, competes for binding to VWF D4 domain with ADAMTS13 as well as with the mAb508 of the invention as defined above and partially inhibits ADAMTS13-mediated degradation of VWF.

Epitope binning can be used to identify antibodies that fall within the scope of the claimed invention. Epitope binning refers to the use of competitive binding assays to identity pairs of antibodies that are, or are not, capable of binding VWF simultaneously, thereby identifying pairs of antibodies that bind to the same or overlapping epitopes on VWF. Epitope binning experiments provide evidence that antigenically distinct epitopes are present. Competition for binding can be evaluated for any pair of antibodies or fragments. For example, using the appropriate detection reagents, the binding specificity of antibodies or binding fragments from any source can be compared to the binding specificity of the monoclonal antibodies disclosed herein. Epitope binning can be performed with "isolated antibodies" or with cell culture supernatants. Frequently, binning is performed with first round clonal supernatants to guide the choice of clones to be developed further. The antibodies to be compared should be substantially homogeneous antigen binding domains. In the case of "bispecific" or "bifunctional" antibodies the binding specificity of the two different binding sites need to be evaluated or binned independently.

The antibodies of the invention may be assayed for specific binding by any method known in the art. Many different competitive binding assay format(s) can be used for epitope binning. The immunoassays which can be used include, but are not limited to, competitive assay systems using techniques such western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well known in the art (see, e.g., Ausubel et al., eds, 1994 Current Protocols in Molecular Biology, Vol. 1, John Wiley & sons, Inc., New York). For example, the BIACORE0 (GE Healthcare, Piscaataway, N.J.) is one of a variety of surface plasmon resonance assay formats that are routinely used to epitope bin panels of monoclonal antibodies. Additionally, routine cross-blocking assays such as those described in Antibodies, A Laboratory Manual, Cold Spring Harbor Laboratory, Ed Harlow and David Lane, 1988, can be performed.

Methods of Producing Antibodies of the Invention:

The antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Accordingly, a further aspect of the invention relates to a nucleic acid sequence encoding an antibody according to the invention.

In a particular embodiment, the invention relates to a nucleic acid sequence encoding the VH domain of the antibody of the invention (SEQ ID NO: 10) or the VL domain of the antibody of the invention (SEQ ID NO: 11) as defined in Table B:

TABLE B

Sequences of mAb508 domains.

| mAb508 domains | Sequences |
|---|---|
| VH | SEQ ID NO: 10<br>ATGAGAGTGCTGATTCTCTTGTGCCTGTTCACAGCCTTTCC<br>TGGTCTCCTGTCTGATGTGCAGCTTCAGGAGTCAGGACCTG<br>ACCTGGTGGAACCTTCTCAGTCACTTTCACTCTCCTGCACT<br>GTCACTGGCTACTCCATCACCAGTGGTTATAGCTGGCACTG<br>GATTCGGCAGTTTCCAGGAAACAAACTGGAATGGCTGGGCT<br>ACATTCACTACAGTGGCACCACTACCTACAACCCATCTCTC<br>CACAGTCGAGTCTCTATCACTCGAGACACGTCCAAGAACCA<br>GTTCTTCCTGCAGTTGAATTCTGTGTCTACTGAGGACACGG<br>CCACATATTTCTGTGGAAGAGAAGGTTACCATTGGGCCAA<br>GGCACCACTCTCACAGTCTCCTCAGCCAAAACGACACCCCC<br>ATCTGTCTATCCACTGGCCCCTGGATCTGCTGCCCAAACTA<br>ACTCCATGGTGACCCTGGGATGCCTGGTCAAGGGCTATTTC<br>CCTGAGCCAGTGACAGTGACCTGGAACTCTGGATCCCTGTC<br>CAGCGGTGTGCACACCTTCCCAGCTGTCCTGCAGTCTGACC<br>TCTACACTCTGAGCAGCTCAGTGACTGTCCCCTCCAGCACC<br>TGGCCCAGCGAGACCGTCACCTGCAACGTTGCCCACCCGGC<br>CAGCAGCACCAAGGTGGACAAGAAAATTGTGCCCAGGGATT<br>GTGGTTGTAAGCCTTGCATATGTACAGTCCCAGAAGTATCA<br>TCTGTCTTCATCTTCCCCCCAAAGCCCAAGGATGTGCTCAC<br>CATTACTCTGACTCCTAAGGTCACGTGTGTTGTGGTAGACA<br>TCAGCAAGGATGATCCCGAGGTCCAGTTCAGCTGGTTTGTA<br>GATGATGTGGAGGTGCACACAGCTCAGACGCAACCCCGGGA<br>GGAGCAGTTCAACAGCACTTTCCGCTCAGTCAGTGAACTTC<br>CCATCATGCACCAGGACTGGCTCAATGGCAAGGAGTTCAAA<br>TGCAGGGTCAACAGTGCAGCTTTCCCTGCCCCCATCGAGAA<br>AACCATCTCCAAAACCAAAGGCAGACCGAAGGCTCCACAGG<br>TGTACACCATTCCACCTCCCAAGGAGCAGATGGCCAAGGAT<br>AAAGTCAGTCTGACCTGCATGATAACAGACTTCTTCCCTGA<br>AGACATTACTGTGGAGTGGCAGTGGAATGGGCAGCCAGCGG<br>AGAACTACAAGAACACTCAGCCCATCATGGACACAGATGGC<br>TCTTACTTCGTCTACAGCAAGCTCAATGTGCAGAAGAGCAA<br>CTGGGAGGCAGGAAATACTTTCACCTGCTCTGTGTTACATG<br>AGGGCCTGCACAACCACCATACTGAGAAGAGCCTCTCCCAC<br>TCTCCTGGTAAATGA |
| VL | SEQ ID NO: 11<br>ATGAAGTTGCCTGTTAGGCTGTTGGTGCTGATGTTCTGGAT<br>TCCTGGTTCCACCAGTGATGTTGTGATGACCCAAACTCCAC<br>TCTCCCTGCCTGTCAGTCTTGGAGATCAAGCCTCCATCTCT<br>TGCAGATCTAGTCAGAGTCTTGTACACAGCATTGGAAACAC<br>CTATTTACATTGGTACCTGCAGAAGCCAGGCCAGTCTCCAA<br>AACTCCTGATCTACAAAGTCTCCAATCGATTTTCTGGGGTC<br>CCAGACAGATTCAGTGGCAGTGGATCAGGGACAGATTTCAC<br>ACTCAAGATCAGCAGAGTGGAGGCTGAGGATCTGGGAGTTT<br>ATTTCTGCTCTCAAACTACACATGTTCCTCTGACGTTCGGT<br>GGAGGCACCAGGTTGGAAATCAAACGGGCTGATGCTGCACC<br>AACTGTATCCATCTTCCCACCATCCAGTGAGCAGTTAACAT<br>CTGGAGGTGCCTCAGTCGTGTGCTTCTTGAACAACTTCTAC<br>CCCAAAGACATCAATGTCAAGTGGAAGATTGATGGCAGTGA<br>ACGACAAAATGGCGTCCTGAACAGTTGGACTGATCAGGACA |

TABLE B-continued

Sequences of mAb508 domains.

| mAb508 domains | Sequences |
|---|---|
| | GCAAAGACAGCACCTACAGCATGAGCAGCACCCTCACGTTG ACCAAGGACGAGTATGAACGACATAACAGCTATACCTGTGA GGCCACTCACAAGACATCAACTTCACCCATTGTCAAGAGCT TCAACAGGAATGAGTGTTAG |

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further aspect of the invention relates to a vector comprising a nucleic acid of the invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of 5V40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further aspect of the invention relates to a host cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

The nucleic acids of the invention may be used to produce an antibody of the invention in a suitable expression system. The term "expression system" means a host cell and compatible vector under suitable conditions, e.g. for the expression of a protein coded for by foreign DNA carried by the vector and introduced to the host cell.

Common expression systems include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like.

The invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the invention.

Antibodies of the invention are suitably separated from the culture medium by conventional immunoglobulin purification procedures such as, for example, protein A-Sepharose, hydroxylapatite chromatography, gel electrophoresis, dialysis, or affinity chromatography.

In a particular embodiment, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell.

As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used.

Methods for producing chimeric antibodies involve conventional recombinant DNA and gene transfection techniques are well known in the art (See Morrison S L. et al. (1984) and patent documents U.S. Pat. Nos. 5,202,238; and 5,204,244).

The humanized antibody of the invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell.

The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred (shiara K et al. 1994). Examples of tandem type humanized antibody expression vector include pKAN-TEX93 (WO 97/10354), pEE18 and the like.

Methods for producing humanized antibodies based on conventional recombinant DNA and gene transfection techniques are well known in the art (See, e. g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

The Fab of the invention can be obtained by treating an antibody which specifically reacts with human VWF with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the invention can be obtained treating an antibody which specifically reacts with human VWF with a protease, pepsin. Also, the F(ab')2 can be produced by binding Fab' described below via a thioether bond or a disulfide bond.

The Fab' of the invention can be obtained treating F(ab')2 which specifically reacts with human VWF with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e. g., WO98/45322; WO 87/02671; U.S. Pat. No. 5,859,205; 5,585,089; 4,816,567; EP0173494).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity. In order to resolve the problem, in antibodies grafted with human CDR, attempts have to be made to identify, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody with desirable characteristics.

In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are:

isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

A further aspect of the invention also encompasses function-conservative variants of the antibodies of the invention.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

Two amino acid sequences are "substantially homologous" or "substantially similar" when greater than 80%, preferably greater than 85%, preferably greater than 90% of the amino acids are identical, or greater than about 90%, preferably grater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said antibodies, without appreciable loss of their biological activity.

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Another type of amino acid modification of the antibody of the invention may be useful for altering the original glycosylation pattern of the antibody.

By "altering" is meant deleting one or more carbohydrate moieties found in the antibody, and/or adding one or more glycosylation sites that are not present in the antibody.

Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as thoseof cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr H. et al. (1987) and by Edge, A S. et al. (1981). Enzymatic cleavage of carbohydrate moieties on antibodies can be achieved by the use of a variety of endo- and exo-glycosidases as described by Thotakura, N R. et al. (1987).

Another type of covalent modification of the antibody comprises linking the antibody to one of a variety of non proteinaceous polymers, eg., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Therapeutic Methods and Uses of the Invention:

Antibodies of the invention are presented to be useful for the prevention or the treatment of bleeding episodes, such as bleeding episodes occurring in conditions characterised by loss of HMW-multimers of VWF caused by increased shear stress. Accordingly, antibodies of the invention are useful for the prevention or the treatment of bleeding episodes, in particular gastrointestinal (GI) bleedings, in patients with aortic stenosis or patients with ventricular assist devices (VAD).

A used herein, the term "bleeding" refers to extravasation of blood from any component of the circulatory system. A "bleeding episode" thus encompasses unwanted, uncontrolled and often excessive bleeding in connection with surgery, trauma, or other forms of tissue damage, as well as unwanted bleedings in patients having bleeding disorders. More particularly, unexplained bleeding episodes are associated with VAD and can occur in part due to acquired von Willebrand syndrome (aVWS). AVWS is characterised by loss of HMW-multimers of VWF. Loss of multimers can occur as VWF is subjected to increased shear stress, which occurs in presence of VADs.

Therapeutic antibodies according to the invention thus lead to the partial inhibition (reduction) of ADAMTS13-mediated degradation of VWF caused by an increased shear stress, thereby inhibiting bleeding episodes in patients in need thereof. Bleeding episodes are a typical complication in patients with extracorporeal life support (ECLS). ECLS is used for patients with refractory heart failure with or without respiratory failure.

According to the invention, the term "patient" or "patient in need thereof" is intended for a human or affected or likely to be affected with bleeding episodes, such as for instance in patients with aortic valve stenosis, leading to gastrointestinal bleeding (Heyde's syndrome), in patients with aVWS and aortic stenosis who underwent valve replacement experienced a correction of their hemostatic abnormalities but that the hemostatic abnormalities can recur after 6 months when the prosthetic valve is a poor match with the patients, in patients with an ECLS such as an implant of a Left Ventricular Assist Device (LVAD), a pump that pumps blood from the left ventricle of the heart into the aorta or patient having extracorporeal membrane oxygenation (ECMO) support. A patient in need thereof also encompasses a patient with hereditary von Willebrand disease type 2A. In Type ha, the ability of the defective VWF form large VWF multimers is also impaired, resulting in decreased quantity of large VWF multimers. Only small multimer units are detected in the circulation.

The term "therapeutically effective amount" is meant for a sufficient amount of antibody in order to treat said disease, at a reasonable benefit/risk ratio applicable to any medical treatment. It will be understood, however, that the total daily usage of the antibodies and compositions of the invention will be decided by the attending physician within the scope of sound medical judgment. The specific therapeutically effective dose level for any particular patient will depend upon a variety of factors including the disorder being treated and the severity of the disorder, activity of the specific antibody employed, the specific composition employed, the age, body weight, general health, sex and diet of the patient, the time of administration, route of administration, and rate of excretion of the specific antibody employed, the duration of the treatment, drugs used in combination or coincidental with the specific polypeptide employed, and like factors well known in the medical arts. For example, it is well known within the skill of the art to start doses of the compound at levels lower than those required to achieve the desired therapeutic effect and to gradually increase the dosage until the desired effect is achieved.

Another aspect of the invention relates to a method for preventing or treating bleeding episodes in a patient in need thereof, comprising a step of administering to said patient a therapeutically effective amount of an antibody or a fragment of the invention to said patient.

Antibodies of the invention may be used in combination with any other therapeutical strategy for treating thrombosis, thrombotic microangiopathy, thrombotic thrombocytopenic purpura, Schulman-Upshaw syndrome, atherosclerosis or acute syndrome diseases (e.g. plasmapharesis). The antibodies of the invention may be used alone or in combination with any suitable agent. For example, the antibodies of the invention may be combined with an anti-platelet agent such as aspirin, P2Y12 ADP receptor antagonist (e.g. clopidogrel) and GPIIbIIIa inhibitors. The antibodies of the invention may also be combined with thrombolytic agent or a recombinant variant or fragment thereof which is selected from the group consisting of staphylokinase, tissue plasminogen activator, streptokinase, single chain streptokinase, urokinase and acyl plasminogen-streptokinase complex.

Pharmaceutical Compositions:

A further aspect of the invention relates to a pharmaceutical composition comprising an antibody or a fragment of the invention.

The nucleic acids, antibodies or fragments of the invention may be combined with pharmaceutically acceptable carriers, and optionally sustained-release matrices, such as biodegradable polymers, to form therapeutic compositions. "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical or therapeutic compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions, formulations including sesame oil, peanut oil or aqueous propylene glycol, and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of micro-organisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of micro-organisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatine.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration, time release capsules, and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to be degraded in vivo. Biodegradable polyalkyl-cyanoacrylate nanoparticles that meet these requirements are contemplated for use in the invention, and such particles may be easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

The invention will be further illustrated by the following figures and examples. However, these examples and figures should not be interpreted in any way as limiting the scope of the invention.

FIGURES

FIG. 1: Screening for competitive inhibitors of VWF-ADAMTS13 binding: Candidate inhibitors were tested in an immuno-sorbent assay evaluating the binding of V5-tagged wt-rADAMTS13 (3 µm/ml) to immobilized pd-VWF (2 µm/mL) in the presence of EDTA (10 mM). (A): Fc- or HPC4-tagged VWF fragments (10 nM) were incubated for 30 minutes at 37° C. with wt-rADAMTS13 before addition to immobilized full-length VWF in microtiter wells for 3 hours. Bound ADAMTS13 was probed using a peroxidase-labeled monoclonal anti-V5 tag antibody for 2 h at 37° C. and detected via peroxidase-mediated hydrolysis of TMB. (B): A panel of mAbs targeting VWF was evaluated for their effect on ADAMTS13 binding to VWF as described for Panel A using polyclonal antibodies as negative (mouse IgG) and positive (rabbit anti-VWF IgG) controls (all antibodies were tested at a concentration of 0.1 mg/ml). Data represent the mean±SD of 3-5 experiments and are expressed as residual ADAMTS13 binding compared to incubation in the absence of VWF-fragments or antibodies for panel A and B, respectively. For panel B, data representing antibodies recognizing different VWF domains (D', A1, A2, A3) are depicted. ***: $p<0.0001$ as calculated via one-way ANOVA with Dunnett-multiple comparison test.

Figure 2:
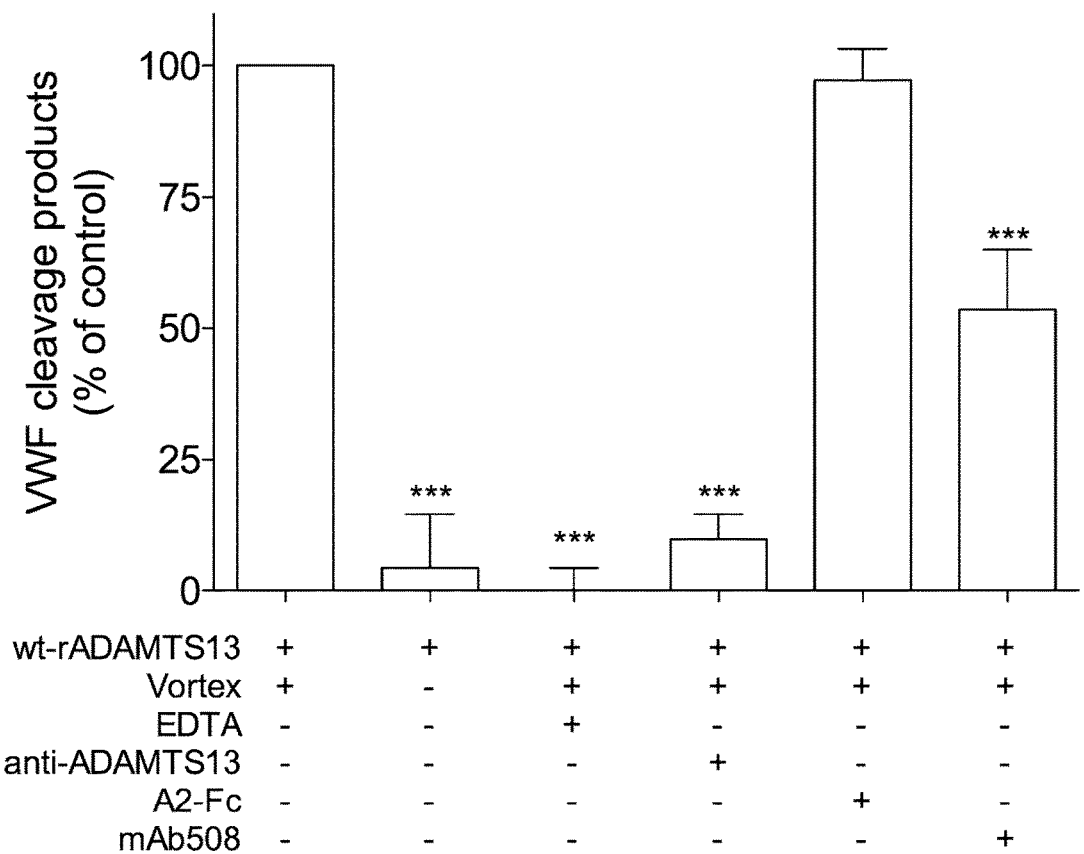

FIG. 2: Functional evaluation of mAb508 and A2-Fc in a vortex-based degradation assay. pd-VWF (30 µm/ml), wt-rADAMTS13 (3 µm/ml) and Pefabloc (2.5 mM) were incubated in a volume of 40 µl and exposed to constant vortexing (Vortex Genie 2T; 2500 rpm) for 60 min in the absence or presence of one the following components: EDTA (10 mM), polyclonal anti-ADAMTS13 antibodies (50 µg/ml), A2-Fc (1 µg/ml) or mAb508 (0.1 mg/ml). VWF and ADAMTS13 were also incubated for 60 min in the absence of vortexing (no shear). VWF degradation was semi-quantified via integration of immuno-precipitated VWF degradation bands (140 & 176 kDa) using ImageJ software. Data represent mean±SD of 4 experiments and are expressed as percentage VWF degradation. Degradation after 60 min vortexing in the absence of additional components added was set at 100%. ***: $p<0.0001$ as calculated via one-way ANOVA with Dunnett-multiple comparison test.

Figure 3:
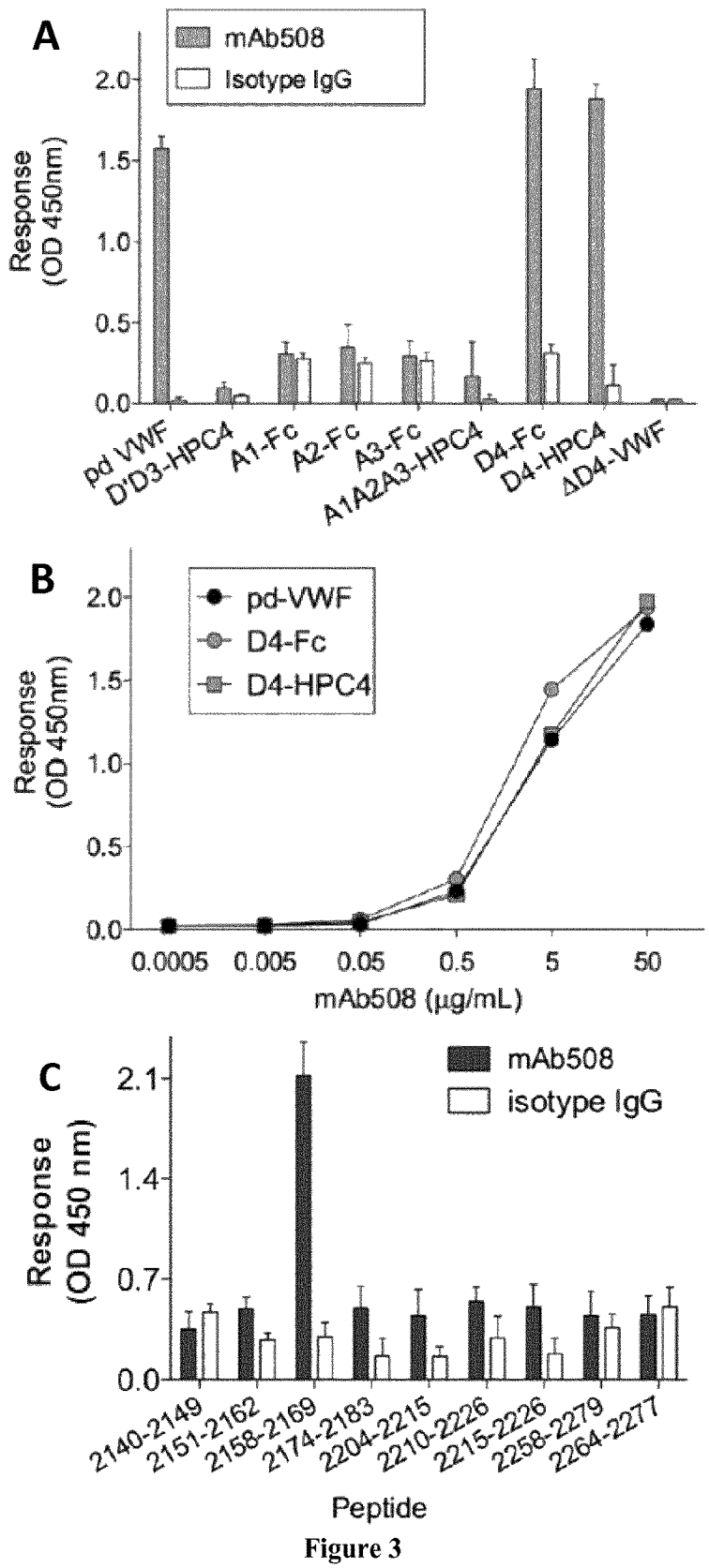

FIG. 3: mAb508 interacts with D4 domain of VWF. (A) & (B): Purified proteins (10 nM) were immobilized onto microtiter wells for 16H at 4° C. After washing, wells were incubated with mAb508 (Panel A: 5 µg/ml; Panel B: 0.5 ng/ml-50 µg/ml) or an isotype mouse IgG control (Panel A: 5 µg/ml) for 1 h at 37° C. Bound antibodies were probed using peroxidase-labeled polyclonal goat anti-mouse IgG antibodies and detected via peroxidase-mediated TMB hydrolysis. (C): Biotinylated-peptides were immobilized onto streptavidin-coated microtiter wells and incubated with mAb508 or isotype mouse IgG (both 5 µg/ml). Bound antibodies were probed and detected as described for A and B. Data in A and C represent mean±SD of 3-5 experiments. For B, data from a single experiment are shown.

Figure 4:
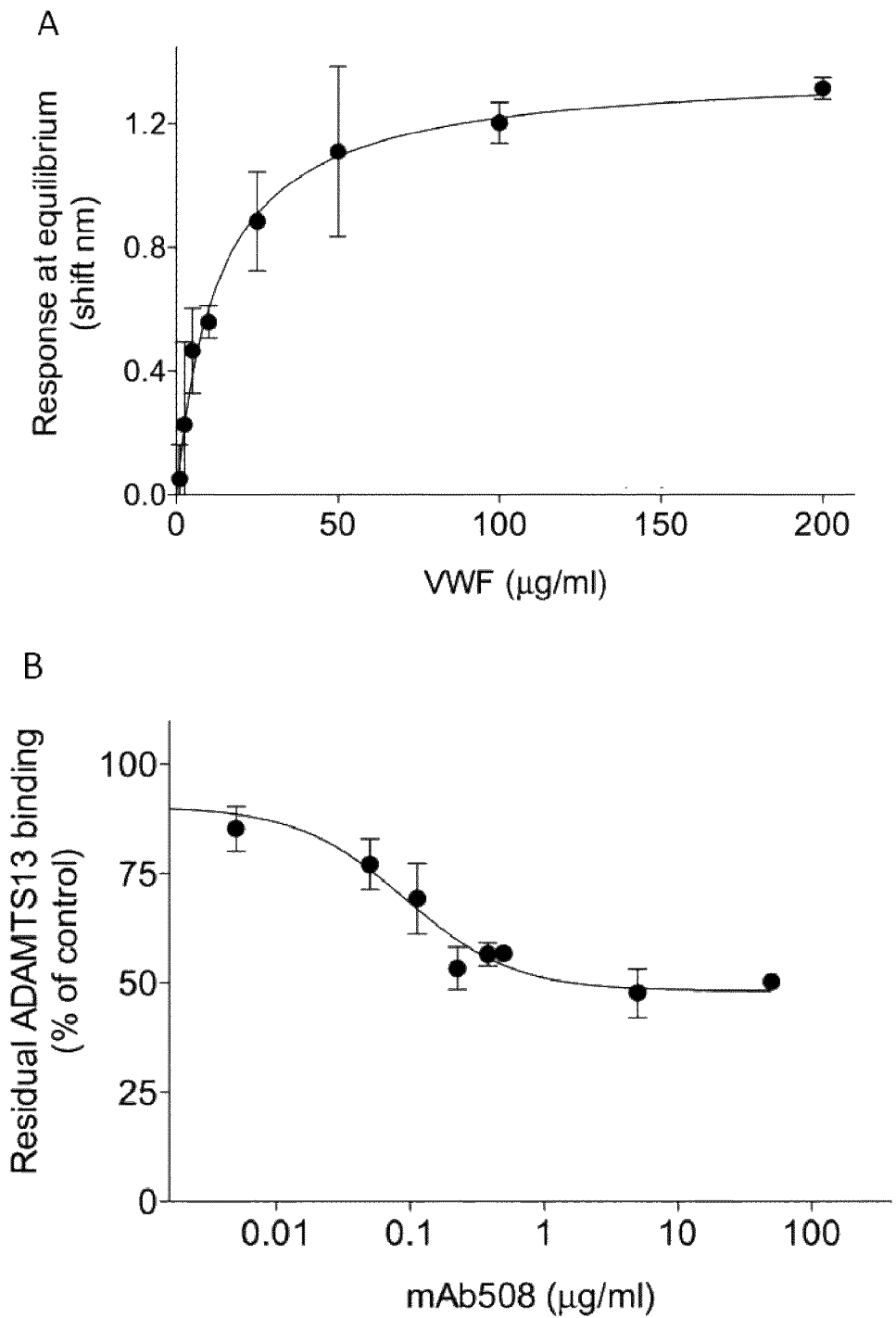

FIG. 4: Biochemical analysis of VWF-mAb508 interaction. (A) Protein A-coated biosensors were saturated with mAb508 (0.5 mg/ml) during a 7 min incubation using Octet-QK equipment. Subsequently, biosensors were incubated with various concentrations purified pd-VWF (0-0.2 mg/ml) and association of VWF was monitored real-time for a 10-min period until equilibrium was reached. Data represent mean±SD of four independent associations and depicted are the calculated responses (shift in nm) at equilibrium versus VWF concentration. The drawn line represents the best fit using a model describing the interaction of a single class of binding sites. (B) Binding of ADAMTS13 to immobilized VWF was performed as described for FIG. 1 in the absence or presence of various concentrations mAb508 (0.05 ng/ml-50 µg/ml). Data represent the mean±SD of four experiments and are expressed as % of residual ADAMTS13 binding compared to the absence of mAb508. Drawn line represents the best fit using a sigmoidal dose-response.

Figure 5:
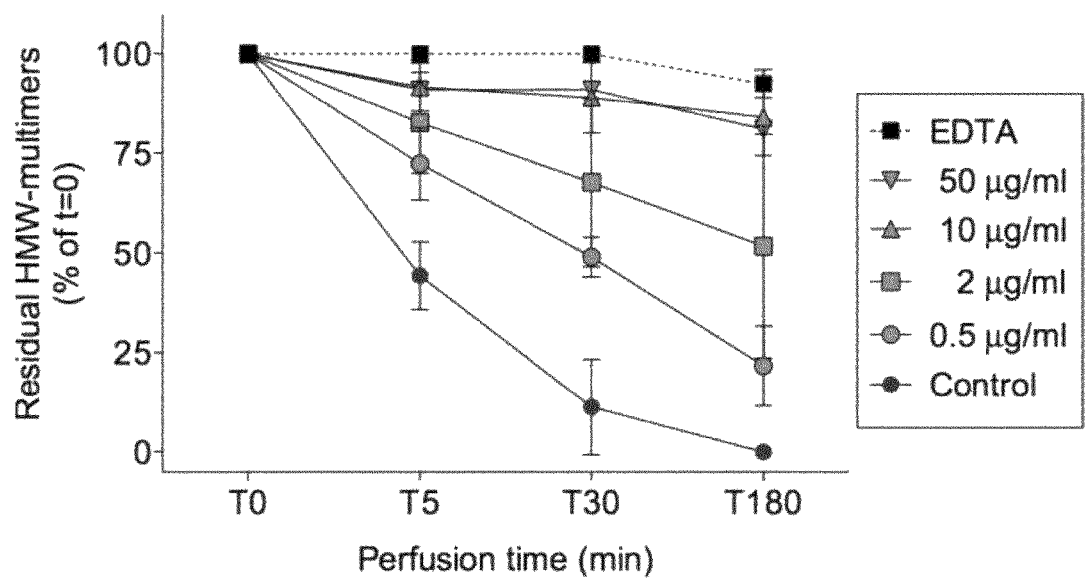

FIG. 5: Evaluation of mAb508 on shear-induced VWF proteolysis in flowing blood. Citrated whole human blood (200 ml) was perfused in an ex vivo perfusion system incorporating a HeartMateII® pump. The pump rotor was set to 9000 rpm. Perfusions were performed in the absence (closed black circles) or presence of EDTA (10 mM; closed black squares) or various concentrations of mAb508 (0.5 µg/ml, grey circles; 2 µg/ml grey squares; 10 µg/ml, grey triangles up; 50 µg/ml, grey triangles down). Samples were taken 5 min before the onset of perfusion (T0) and after 5 min (T5), 30 min (T30) or 180 min (T180). Samples were subsequently tested for multimer patterns via 1.4% SDS-agarose electrophoresis and the presence of HMW-multimers (>15-mers) was determined. Presence of HMW-multimers (percentage of HMW-multimers compared to T0, which was set at 100%) as a function of time.

EXAMPLE: ROLE OF ANTI-HUMAN VON WILLEBRAND FACTOR MONOCLONAL ANTIBODY 508 IN PREVENTION OF EXCESSIVE VWF DEGRADATION IN A WHOLE BLOOD-PERFUSION MODEL

Material & Methods

Proteins: Purified plasma-derived (pd)-VWF and recombinant (r)-VWF were obtained as described previously (25, 26). All r-VWF fragments were produced using stably transfected BHK-cell lines. Transfection was performed using pNUT- or pFUSE-plasmids that contained synthetic cDNA sequences. cDNAs cloned into pNUT contained a 5'-sequence encoding the VWF signal peptide to allow secretion and a 3'-sequence encoding the HPC4 recognition motif D'D3-HPC4 was obtained via the expression of a pNUT-plasmid encoding VWF-residues 1-1247. The purified protein lacks the VWF propeptide (residues 1-763) and is dimeric. A1A2A3-HPC4 and D4-HPC4 include VWF-residues 1261-1872 and 1947-2301, respectively. HPC4-tagged proteins were purified to homogeneity using HPC4-immuno affinity chromatography as instructed by the manufacturer (Roche Diagnostics, Meylan, France). A1-Fc, A2-Fc, A3-Fc and D4-Fc include VWF residues 1261-1478, 1480-1672, 1681-1878 and 1947-2301, respectively. A13-1-685-Fc includes residues 1-685 of ADAMTS13. All proteins expressed using the pFUSE contained a C-terminal Fc sequence of human IgG1 and were dimeric. Fc-tagged proteins were purified to homogeneity using protein A-Sepharose as instructed by the manufacturer (VWR International, Fontenay-sous-Bois, France). A panel of 29 monoclonal murine antibodies against human VWF was established in the 1980s (27, 28). Monoclonal antibodies were purified to homogeneity as described (27). Recombinant wild-type ADAMTS13 (wt-rADATMS13) containing a V5- and a His-tag was produced as described (29). Conditioned medium enriched in wt-rADAMTS13 that was concentrated 5-fold using an Amicon Ultra-15 centrifugal filter unit with a Ultracel-30K membrane (Millipore, Molsheim, France) and extensively dialyzed against 50 mM Tris, pH 7.4 was used throughout the study. Bovine Serum Albumin (BSA) was obtained from Sigma-Aldrich (Saint-Quentin Fallavier, France).

Binding of wt-rADAIVITS13 to VWF: pd-VWF (2 µg/ml) was adsorbed to microtiter wells. After blocking with BSA-containing buffer, immobilized VWF was incubated with supernatant containing wt-rADAMTS13 (3 µg/ml) supplemented with EDTA (10 mM) and Pefabloc (10 mM) for 3 h at 37° C. Bound wt-rADAMTS13 was probed using a peroxidase-labeled monoclonal anti-V5 tag antibody (Abcys, Paris, France) for 2 h at 37° C. and detected via peroxidase-mediated hydrolysis of tetramethylbenzidine (TMB). VWF fragments (10 nM final concentration, unless indicated otherwise) or anti-VWF antibodies (0.1 mg/ml final concentration, unless indicated otherwise) were pre-incubated with wt-rADAMTS13 for 30 min at room temperature before addition to VWF containing microtiter wells.

Vortex-based VWF degradation assay: Vortex-based degradation of VWF was essentially performed as described (30). Briefly, purified pd-VWF (30 µg/ml), wt-rADAMTS13 (3 µg/ml) and Pefabloc (2.5 mM; Sigma-Aldrich) were incubated in a volume of 40 µl and exposed to constant vortexing (2500 rpm; Vortex Genie 2T; VWR International) for indicated time points. Where indicated, samples were supplemented with EDTA (10 mM), polyclonal goat anti-ADAMTS13 antibodies (50 µg/ml), A2-Fc (1 µg/ml) or mAb508 (0.1 mg/ml). VWF degradation was assessed via Western blot analysis, which was preceded by immuno-precipitation using anti-VWF antibodies where indicated. VWF was immuno-precipitated using rabbit polyclonal anti-VWF antibodies (50 µg/ml beads; Dako, Glostrup, Danmark) adsorbed onto Protein-G-coated magnetic beads (Dynabeads Protein G, Invitrogen, Saint Aubin, France) for 2 h at room temperature. After extensive washing in PBS/0.1% Tween-20, immunoprecipitated VWF was released from the beads via a 5 min incubation at 100° C. in 30 µl PBS/10 µl NuPAGE-LDS 4× sample buffer (Life Technologies, Saint Aubin, France) in the presence of 2 mM dithiothreitol. Samples were separated via discontinuous 4-12% SDS-page (Invitrogen) and transferred to an Immobilon P membrane (Millipore, Molsheim, France). The presence of VWF or degradation fragments was revealed via incubation with a pool of 10 distinct monoclonal antibodies recognizing distinct epitopes of VWF (10 µg/ml). Bound antibodies were probed using peroxidase-labeled goat anti-mouse antibodies (dilution 1:500; Santa Cruz, Heidelberg, Germany) and visualized with SuperSignal West-Pico Enhanced Chemiluminescence Substrate (Thermo-Fischer Scientific, Villebon-sur-Yvette, France). Blots were analyzed via ImageJ-1.44 software (http://rsbweb.nih.gov/ij/index.html) in order to quantify increase in VWF degradation products (represented by the presence of 140 kDa and 176 kDa bands) relative to untreated VWF.

Antibody binding to synthetic peptides: A series of 9 highly purified (>95%) synthetic peptides overlapping various hydrophilic motifs of the D4 domain region 2140-2277 containing a N-terminal biotin tag were obtained from EZBiolab (Carmel, Ind.). Peptides were solubilized in $H_2O$, eventually supplemented with one-sixth volume of 10% $NH_4OH$ to improve solubility if necessary. Peptides were immobilized onto streptavidin-coated microtiter plates (SigmaScreen Streptavidin High Capacity, Sigma-Aldrich) at a concentration of 50 µg/ml. Peptide-coated wells were incubated with mAb508 or mouse isotype IgG (5 µg/ml) in PBS containing 3% BSA. Bound antibody was probed using peroxidase-labeled polyclonal anti-mouse IgG and detected via peroxidase-mediated hydrolysis of TMB.

Biolayer interferometry-analysis: Equilibrium binding assays were performed via biolayer interferometry (BLI)-analysis using Octet-QK equipment (ForteBio, Reading, UK) essentially as described (26). Protein A-coated biosensors were incubated with mAb508 (0.5 mg/ml) in BLI-buffer (PBS/2% BSA) for 7 min allowing saturation of the sensor. Biosensors were then incubated for 5 min in BLI-buffer to achieve stable baseline, and subsequently incubated with various concentrations of pd-VWF in BLI-buffer for 10 min. All incubations were performed at room temperature under continuous shaking (1000 rpm). Data were analyzed using Octet Software version 4.0.

Ex vivo whole blood perfusion: The perfusion system consisted of a circulatory flowing pump device in which the HeartMateHO (Thoratec Corp., Pleasanton, Calif.) was the pump. Two cylindrical tubings (1×2×3/32 xs; Sorin group Implant®) were used to connect the device. The inlet and outlet ducts of the HeartMateII® were connected with these two tubings to obtain a closed circuit, which further contained a sampling device. The distribution volume was approximately 250 ml. The system was filled with citrate-anticoagulated whole blood (Blood group O) provided by the local blood bank (Etablissement Francais du Sang, Lille, France). Where indicated, blood was supplemented with EDTA (10 mM final concentration) or antibody mAb508 (0.5-50 µg/ml final concentration). The pump rotor was set at 9000 rpm, a speed that is normally applied upon patient use (31). Blood was sampled 5 min before onset of perfusion (T0) and 5, 30 and 180 minutes after onset of perfusion (T5, T30 and T180, respectively). Blood samples were analyzed for multimeric profile via 1.4% SDS-agarose electophoresis as described (18). Analysis of loss of high molecular weight (HMW)-multimers was measured and calculated as described (18).

Results

Selection of candidates inhibiting VWF-ADAMTS3 interactions: To select potential inhibitors of VWF proteolysis, we first tested candidate molecules in an immunosorbent assay assessing binding of ADAMTS13 to immobilized VWF in the presence of EDTA. In this assay, immobilized VWF is elongated and exposes its interactive sites for ADAMTS13, including those localized within the VWF A2 domain (8). Two distinct types of potential inhibitors were evaluated. First, the potential of several monomeric or dimeric VWF-derived fragments (C-terminally tagged with either the HPC4-recognition sequence or with Fc) to block VWF-ADAMTS13 interactions was tested (FIG. 1A). When analyzed at a concentration of 10 nM, the majority of them (D'D3-HPC4, A1-Fc, A3-Fc, A1A2A3-HPC4 and D4-Fc) exhibited minor inhibition (≤20%), whereas dimeric A2-Fc displayed substantial inhibition at this concentration (65±6%; n=5; p<0.001). We next assessed a panel of murine monoclonal antibodies (0.1 mg/ml) directed either against VWF or ADAMTS13 (FIG. 1B). Control experiments showed that ADAMTS13 binding was markedly inhibited in the presence of polyclonal anti-VWF antibodies (75±9%; n=3; p<0.0001), whereas binding was unaffected in the presence of control mouse IgG. None of our 3 monoclonal anti-ADAMTS13 antibodies proved inhibitory (data not shown). Among the 29 monoclonal anti-VWF antibodies tested, 18 mAbs were unable to inhibit VWF-ADAMTS13 interactions, whereas 10 antibodies displayed mild inhibition (<15%). In FIG. 1B, representative data for antibodies recognizing different VWF domains (D', A1, A2, A3) are depicted. The strongest inhibitor was antibody mAb508, which reduced binding of ADAMTS13 to VWF by 46±14% (n=5; p<0.0001). Taken together, these data identify the A2-Fc fragment and antibody mAb508 as potential inhibitors of the VWF-ADAMTS13 interaction.

mAb 508 reduces vortex shear stress-induced VWF proteolysis: Fluid shear stress plays a critical role in regulating ADAMTS13-mediated proteolytic cleavage of soluble VWF by ADAMTS13. Therefore, we tested the inhibitory effect of mAb508 (0.1 mg/ml) and A2-Fc (1 µg/ml), under conditions of increased shear stress, using a vortex-based degradation assay (30). VWF degradation was monitored using densitometric integration of VWF cleavage products (140 & 176 kDa) obtained after immunoprecipitation and western-blot analysis. In our experimental conditions, proteolytic cleavage of pd-VWF (30 µg/ml) by recombinant ADAMTS13 (3 µg/ml) increases as a function of incubation time, with maximal degradation obtained after 30 min. In subsequent experiments, we incubated for 60 min to ensure maximal degradation. Importantly, degradation of VWF by the metalloprotease ADAMTS13 was inhibited by the addition of the chelator EDTA (10 mM) or polyclonal goat anti-human ADAMTS13 antibodies (residual proteolysis <10% compared to control; FIG. 2). Furthermore, no VWF proteolysis was observed in the absence of shear stress. Unexpectedly, VWF proteolysis was unaffected (residual proteolysis 96±5%; n=3) by the addition of A2-Fc (1 µg/ml), despite the notion that this fragment interferes with VWF-ADAMTS13 interactions under static conditions. In contrast, degradation of VWF was markedly reduced (residual proteolysis 52±10% compared to control; n=4; p<0.0001) in the presence of mAb508 (0.1 mg/ml). This indicates that the monoclonal anti-VWF antibody mAb508 is able to partially interfere with ADAMTS13-mediated proteolysis under conditions of increased shear stress.

The epitope for mAb508 is located in the VWF D4 domain: To identify the epitope of mAb508, we first evaluated binding of the antibody to distinct VWF fragments in an immuno dot-blot assay, in which bound antibody was probed using peroxidase-conjugated polyclonal goat anti-mouse antibodies. As expected, mAb508 interacted with both r-VWF and pd-VWF that were used as positive controls. No signal was observed for HPC4-tagged constructs D'D3-HPC4 and A1A2A3-HPC4, whereas a weak signal was present for Fc-tagged variants A1-Fc, A2-Fc and A3-Fc. A similar weak signal was observed with a control Fc-fragment containing residues 1-685 of ADAMTS13, suggesting a minor cross-reaction of the anti-mouse IgG with human Fc fragments. Conversely, mAb508 strongly bound to two different fragments that contained the D4 sequence (VWF residues 1947-2301), i.e. monomeric D4-HPC4 and dimeric D4-Fc. A similar specificity for VWF D4 domain was observed in an immuno-sorbent assay (FIG. 3A). Indeed, no binding was observed with VWF fragments lacking the D4 domain, including a D4 domain-deleted VWF variant. In contrast, a strong positive signal was observed for the binding of mAb508 to pd-VWF and both D4 fragments (FIG. 3A). Moreover, similar dose-response curves were observed for the binding of mAb508 to immobilized D4 fragments and pd-VWF, suggesting that the D4 domain contains the full epitope for mAb508 (FIG. 3B). In order to define the mAb508 epitope in the VWF D4 domain, we next tested binding of the antibody to VWF fragments obtained via proteolysis by Staphylococcus aureus V-8 protease, which cleaves within the D4 domain between residues 2133 and 2134 (32). mAb508 reacted exclusively with the SPII fragment (residues 2134-2813) but not with the SPIII fragment (764-2133) (data not shown), narrowing the antibody's epitope to the distal part of the D4 domain, i.e. residues 2134-2301. To obtain more detailed information on the epitope localization, we used a series of 9 biotinylated-peptides encompassing hydrophilic regions of the distal D4 domain. Using this approach, we observed that mAb508 bound to a single peptide covering residues 2158 to 2169 (FIG. 3C). In conclusion, the epitope of mAb508 appears to be located within the VWF D4 domain, a region previously found to be of relevance for the VWF-ADAMTS13 interaction (6, 8).

mAb508 is a partial inhibitor of VWF-ADAMTS13 interactions: To further characterize the mAb508-VWF interaction, the apparent binding affinity was determined. Interactions between mAb508 and globular full-length VWF were assessed via bio-layer interferometry analysis using Octet-QK-equipment. Increasing concentrations of purified pd-VWF (0 to 0.2 mg/ml) were incubated with mAb508 immobilized onto protein A-biosensor tips. A time- and dose-dependent association of pd-VWF to mAb508 was observed. (In order to calculate the apparent affinity, responses at equilibrium (Bmax) were plotted versus VWF concentrations. Best fitting of the data was obtained using a model describing the interaction of a single class of binding sites (FIG. 4A), which revealed a $K_{D,app}$ of 13±3 µg/ml (mean±SD), corresponding to 52±11 nM based on VWF monomer concentrations. We next investigated the inhibitory potential of mAb508 for the VWF-ADAMTS13 interaction in a competitive VWF-ADAMTS13 inhibition binding assay. VWF was directly coated (2 µg/ml) into a microtiter plate and increasing concentrations of mAb508 (range: 0 to 50 µg/ml) were used as competitor of ADAMTS13 (4 µg/ml). A dose-dependent inhibition was observed (FIG. 4B). mAb508 inhibited the binding of soluble ADAMTS13 to immobilized VWF with an estimated $IC_{50}$ of 0.09±0.03 µg/ml. Maximal inhibition was obtained using 0.5 µg/ml of antibody and did not exceed 50% even when using antibody concentrations up to 50 µg/ml (FIG. 4B). In conclusion, mAb508 binds to VWF with moderate affinity, and its binding to VWF partially inhibits the interaction between VWF and ADAMTS13.

mAb508 reduces shear stress-induced VWF proteolysis under conditions of flow: To evaluate whether mAb508 could represent a potential tool to inhibit degradation of HMW-multimers in patients with VAD, we used an ex vivo perfusion system incorporating the circulatory support pump Heartmate IED. Perfusion of citrated whole blood using this device results in a time-dependent loss of high molecular weight (HMW)-multimers (defined as >15 bands), a phenomenon also observed in patients carrying this device (19). Densitometric analysis revealed a 50% loss of HMW-multimers was observed at 5 min after initiation of the perfusion, and a >95% loss of HMW-multimers occurred after 3 h of perfusion (FIG. 5). In the presence of the chelator EDTA, HMW-multimers remained stable, with only a marginal loss (7±3%) observed after 3 h of perfusion under pathological high shear stress (FIG. 5). Using increasing concentrations of mAb508 (range: 0.5-50 µg/ml; n=3 for each concentration), a dose-dependent mAb-based inhibition of VWF proteolysis was observed at each of the time points analyzed (FIG. 5). A similar extent of inhibition was observed for antibody concentrations of 10 and 50 µg/ml, indicating that maximal inhibition was achieved at 10 µg/ml. Importantly, inhibition was partial in both cases, as a 20% loss of HMW-multimers was detected after 3 h perfusion for each of these antibody concentrations (FIG. 5), consistent with the partial inhibitory potential of mAb508 in the binding experiments. In conclusion, our findings describe the identification of antibody mAb508 as a partial inhibitor of ADAMTS13-mediated degradation of VWF, preventing excessive VWF proteolysis in whole blood under flowing conditions.

Effect of mAb508 on VWF function: To test the effect of mAb508 on VWF-platelet interactions, a ristocetin-based platelet agglutination assay was performed. Platelet-poor plasma of individual donors (supplemented with 0 or 50 µg/ml mAb508) was incubated with formalin-fixed platelets (BC Von Willebrand factor Reagent; Dade Behring/Siemens, Marburg, Germany) as instructed by the manufacturer. Platelet agglutination was initiated by the addition of ristocetin (final concentration 1 mg/ml; Diagnostica Stago; Asnieres, France) and the extent of platelet agglutination was determined via turbidimetric measurements. Experiments were performed in triplicate using plasma of three different donors. Thus, the presence of mAb508 did not affect VWF ristocetin activity, indicating that mAb508 leaves interactions between VWF and platelets unaffected.

Discussion:

Bleeding secondary to increased VWF degradation is currently the leading complication in patients undergoing LVAD support (33) and points to an emerging medical need for a treatment preventing proteolysis of VWF. The most likely candidate responsible for shear stress-induced VWF degradation is ADAMTS13, although a contribution of other proteases cannot be fully excluded (34). Given that a lack of ADAMTS13 activity is associated with TTP, it is further important to consider that blocking VWF proteolysis should be incomplete in order to avoid TTP-like complications. In search for proteolysis inhibitors, we evaluated distinct candidates aiming to disrupt binding of ADAMTS13 to the VWF A2 or D4 domain, two interactive sites necessary to allow VWF proteolysis (6). Among these candidates, one mAb targeting the VWF D4 domain was identified to combine the desired properties of a potential therapeutic candidate, as it partially inhibited VWF-ADAMTS13 binding and reduced but not fully inhibited loss of HMW multimers under conditions of high shear stress.

As expected, our screening of inhibitors of ADAMTS13-mediated proteolysis revealed that a recombinant A2-Fc variant was efficient in interfering with VWF-ADAMTS13 binding, achieving 65% inhibition while a 2-fold molar excess of ADAMTS13 over A2-Fc was present (FIG. 1). This inhibitory action fits with the localization of the Tyr1605-Met1606 scissile bond and additional interactive sites within the VWF A2-domain. The exposure of these A2-domain interactive sites is shear stress-dependent for full-length VWF, but appears to be constitutive for the tested A2-Fc fragment. However, A2-Fc (used at a concentration of 1 µg/ml, corresponding to 10 nM) was unable to prevent VWF degradation under conditions of increased shear stress, suggesting that the scissile bond within the A2-Fc fragment is rapidly cleaved under these conditions thereby reducing the inhibitory potential of this fragment (FIG. 2). Indeed, it has previously been reported that peptides overlapping the C-terminal part of VWF A2 domain interfere with VWF proteolysis at micromolar concentrations, indicating that such fragments are relatively weak inhibitors (35). Additional experiments would therefore be needed to test the inhibitory effect of A2-Fc at higher concentrations. An alternative approach could be to block A2 domain-ADAMTS13 interactions using anti-A2 domain antibodies, as was described elsewhere (36) or antibodies targeting ADAMTS13 epitopes that overlap the A2-interactive site, including the ADAMTS13 spacer domain. However, this ADAMTS13 spacer domain contains the core antigenic epitope of anti-ADAMTS13 auto-antibodies known to be associated with acquired autoimmune TTP (37, 38). Hence, such approach might be associated with an increased risk of drug-induced TTP.

Besides the VWF A2 domain, the VWF D4 domain is also an attractive target to block ADAMTS13-mediated proteolysis. Indeed, the VWF D4 domain contains an exosite accessible on globular VWF, mediating the initial step in the association between VWF and ADAMTS13 (8, 9). However, opposite to the A2-Fc fragment, no inhibition of VWF-ADAMTS13 binding was observed using a D4-Fc fragment (FIG. 1). We considered the possibility that D4-Fc was folded incorrectly. However, D4-Fc displayed similar binding as full length VWF to three distinct anti VWF D4-domain Abs (FIG. 3 & data not shown), indicating that its folding was within the normal range. More likely, D4-Fc is simply inefficient in its interaction with ADAMTS13. This possibility is consistent with the low affinity ($K_{D,app}$=0.7 µM) that was previously reported for the interaction between the isolated VWF D4 domain and ADAMTS13 (8).

Unlike the D4-Fc fragment, binding was efficiently inhibited in the presence of a murine mAb directed against VWF D4 domain (designated as mAb508). The epitope for mAb508 is localized between residues 2134 and 2301 and seems to involve the sequence 2158-2169 (FIG. 3). mAb508 binds the VWF D4 domain with a moderate affinity ($K_{D,app}$=52 nM; FIG. 4A). This value should be considered as an estimate in view of the multimeric structure of VWF and the dimeric nature of the mAb, which complicate an accurate assessment of the true affinity constant. Despite its moderate affinity, mAb508 was particularly efficient to block VWF-ADAMTS13 binding under the conditions employed. Additional experiments are needed to reveal the nature of the inhibitory mechanism, whether inhibition is allosteric or involves direct competition for overlapping binding sites.

In order to assess the clinical potency of the use of anti-D4 domain antibodies to prevent excessive VWF degradation under LVAD support, we implemented a novel LVAD-perfusion model (FIG. 5). This model faithfully mimics the clinical setting, since all experiments are performed in citrated whole blood in the presence of physiological concentrations of VWF and ADAMTS13. Furthermore, unlike vortex-based degradation assays (30), there is no volume limitation allowing more flexibility with regard to spiking experiments with inhibitors and allowing time-course studies with several blood samplings. Using this LVAD-based perfusion model, a dose-dependent inhibition of HMW-multimer degradation was obtained with mAb508, consistent with the marked inhibition obtained in the vortex-based degradation assay (FIGS. 2 & 5). Antibody mAb508 shares it specificity for the D4 domain with antibody RU8, which was recently reported to interfere with ADAMTS13-mediated degradation of VWF in a vortex-based degradation assay (8). However, degradation of HMW-multimers was fully repressed in the presence of 25 µg/ml of antibody RU8, whereas residual VWF proteolysis was still detectable at mAb508 concentrations of 45 µg/ml, indicating fundamental differences in their mode of action. The inability of mAb508 to fully inhibit VWF proteolysis, even in the presence of a vast molar excess, not only fits the requirement for partial inhibition in order to avoid TTP-like symptoms, but also allows for a wide therapeutic window.

In conclusion, we provide an ex vivo proof-of-concept for an antibody-based therapy for the treatment of VWF degradation induced by circulatory assist devices. Such antibody-based treatment could be of benefit not only in VAD, but also in other pathologies characterized by increased VWF proteolysis like aortic stenosis or hypertrophic obstructive cardiomyopathy complicated by Heyde syndrome (18, 39), VWD-type 2A (40), essential thrombocytemia (41) or extracorporeal membrane oxygenation support (42). Such therapy has to compel with the challenging double-edge sword raised by LVAD therapy associated with both significant risks of bleeding and thrombosis. Further experiments are needed in vivo to confirm both the efficiency and the safety of this approach.

REFERENCES

Throughout this application, various references describe the state of the art to which this invention pertains. The disclosures of these references are hereby incorporated by reference into the present disclosure.

1. Zhou Y F, Eng E T, Zhu J, et al. Sequence and structure relationships within von Willebrand factor. Blood 2012; 120(2): 449-58.
2. Sadler J E. von Willebrand factor assembly and secretion. J Thromb Haemost 2009; 7 Suppl 1: 24-7.
3. Valentijn K M, Sadler J E, Valentijn J A, et al. Functional architecture of Weibel-Palade bodies. Blood 2011; 117(19): 5033-43.
4. Groot E, Fijnheer R, Sebastian S A, et al. The active conformation of von Willebrand factor in patients with thrombotic thrombocytopenic purpura in remission. J Thromb Haemost 2009; 7(6): 962-9.
5. De Ceunynck K, De Meyer S F, Vanhoorelbeke K. Unwinding the von Willebrand factor strings puzzle. Blood 2013; 121(2): 270-7.
6. Crawley J T, de Groot R, Xiang Y, et al. Unraveling the scissile bond: how ADAMTS13 recognizes and cleaves von Willebrand factor. Blood 2011; 118(12): 3212-21.
7. Gao W, Anderson P J, Majerus E M, et al. Exosite interactions contribute to tension-induced cleavage of von Willebrand factor by the antithrombotic ADAMTS13 metalloprotease. Proc Natl Acad Sci USA 2006; 103(50): 19099-104.
8. Zanardelli S, Chion A C, Groot E, et al. A novel binding site for ADAMTS13 constitutively exposed on the surface of globular VWF. Blood 2009; 114(13): 2819-28.
9. Feys H B, Anderson P J, Vanhoorelbeke K, et al. Multi-step binding of ADAMTS-13 to von Willebrand factor. J Thromb Haemost 2009; 7(12): 2088-95.
10. Xiang Y, de Groot R, Crawley J T, et al. Mechanism of von Willebrand factor scissile bond cleavage by a disintegrin and metalloproteinase with a thrombospondin type 1 motif, member 13 (ADAMTS13). Proc Natl Acad Sci USA 2011; 108(28): 11602-7.
11. Tsai H M. von Willebrand factor, shear stress, and ADAMTS13 in hemostasis and thrombosis. ASAIO J 2012; 58(2): 163-9.
12. Dong J F, Moake J L, Nolasco L, et al. ADAMTS-13 rapidly cleaves newly secreted ultralarge von Willebrand factor multimers on the endothelial surface under flowing conditions. Blood 2002; 100(12): 4033-9.
13. De Ceunynck K, Rocha S, Feys H B, et al. Local elongation of endothelial cell-anchored von Willebrand factor strings precedes ADAMTS13 protein-mediated proteolysis. J Biol Chem 2011; 286(42): 36361-7.
14. Shim K, Anderson P J, Tuley E A, et al. Platelet-VWF complexes are preferred substrates of ADAMTS13 under fluid shear stress. Blood 2008; 111(2): 651-7.

15. Levy G G, Nichols W C, Lian E C, et al. Mutations in a member of the ADAMTS gene family cause thrombotic thrombocytopenic purpura. Nature 2001; 413(6855): 488-94.

16. Sadler J E, Budde U, Eikenboom J C, et al. Update on the pathophysiology and classification of von Willebrand disease: a report of the Subcommittee on von Willebrand Factor. J Thromb Haemost 2006; 4(10): 2103-14.

17. Warkentin T E, Moore J C, Morgan D G. Aortic stenosis and bleeding gastrointestinal angiodysplasia: is acquired von Willebrand's disease the link? Lancet 1992; 340(8810): 35-7.

18. Vincentelli A, Susen S, Le Tourneau T, et al. Acquired von Willebrand syndrome in aortic stenosis. N Engl J Med 2003; 349(4): 343-9.

19. Geisen U, Heilmann C, Beyersdorf F, et al. Non-surgical bleeding in patients with ventricular assist devices could be explained by acquired von Willebrand disease. Eur J Cardiothorac Surg 2008; 33(4): 679-84.

20. Uriel N, Pak S W, Jorde U P, et al. Acquired von Willebrand syndrome after continuous-flow mechanical device support contributes to a high prevalence of bleeding during long-term support and at the time of transplantation. J Am Coll Cardiol 2010; 56(15): 1207-13.

21. Crow S, John R, Boyle A, et al. Gastrointestinal bleeding rates in recipients of nonpulsatile and pulsatile left ventricular assist devices. J Thorac Cardiovasc Surg 2009; 137(1): 208-15.

22. Pareti F I, Lattuada A, Bressi C, et al. Proteolysis of von Willebrand factor and shear stress-induced platelet aggregation in patients with aortic valve stenosis. Circulation 2000; 102(11): 1290-5.

23. Meyer A L, Malehsa D, Bara C, et al. Acquired von Willebrand syndrome in patients with an axial flow left ventricular assist device. Circ Heart Fail 2010; 3(6): 675-81.

24. Thompson J L, 3rd, Schaff H V, Dearani J A, et al. Risk of recurrent gastrointestinal bleeding after aortic valve replacement in patients with Heyde syndrome. J Thorac Cardiovasc Surg 2012; 144(1): 112-6.

25. Lenting P J, Westein E, Terraube V, et al. An experimental model to study the in vivo survival of von Willebrand factor. Basic aspects and application to the R1205H mutation. J Biol Chem 2004; 279(13): 12102-9.

26. Pegon I N, Kurdi M, Casari C, et al. Factor VIII and von Willebrand factor are ligands for the carbohydrate-receptor Siglec-5. Haematologica 2012; 97(12): 1855-63.

27. Meyer D, Zimmerman T S, Obert B, et al. Hybridoma antibodies to human von Willebrand factor. I. Characterization of seven clones. Br J Haematol 1984; 57(4): 597-608.

28. Meyer D, Baumgartner H R, Edginton T S. Hybridoma antibodies to human von Willebrand factor. II. Relative role of intramolecular loci in mediation of platelet adhesion to the subendothelium. Br J Haematol 1984; 57(4): 609-20.

29. Rayes J, Hommais A, Legendre P, et al. Effect of von Willebrand disease type 2B and type 2M mutations on the susceptibility of von Willebrand factor to ADAMTS-13. J Thromb Haemost 2007; 5(2): 321-8.

30. Han Y, Xiao J, Falls E, et al. A shear-based assay for assessing plasma ADAMTS13 activity and inhibitors in patients with thrombotic thrombocytopenic purpura. Transfusion 2011; 51(7): 1580-91.

31. Frazier O H, Delgado R M, 3rd, Kar B, et al. First clinical use of the redesigned HeartMate II left ventricular assist system in the United States: a case report. Tex Heart Inst J 2004; 31(2): 157-9.

32. Layet S, Girma J P, Obert B, et al. Evidence that a secondary binding and protecting site for factor VIII on von Willebrand factor is highly unlikely. Biochem J 1992; 282 (Pt 1): 129-37.

33. Eckman P M, John R. Bleeding and thrombosis in patients with continuous-flow ventricular assist devices. Circulation 2012; 125(24): 3038-47.

34. Lancellotti S, Basso M, De Cristofaro R. Proteolytic Processing of Von Willebrand Factor by Adamts13 and Leukocyte Proteases. Mediterr J Hematol Infect Dis 2013; 5(1): e2013058.

35. Wu J J, Fujikawa K, McMullen B A, et al. Characterization of a core binding site for ADAMTS-13 in the A2 domain of von Willebrand factor. Proc Natl Acad Sci USA 2006; 103(49): 18470-4.

36. Zhang J, Ma Z, Dong N, et al. A conformation-sensitive monoclonal antibody against the A2 domain of von Willebrand factor reduces its proteolysis by ADAMTS13. PLoS One 2011; 6(7): e22157.

37. Klaus C, Plaimauer B, Studt J D, et al. Epitope mapping of ADAMTS13 autoantibodies in acquired thrombotic thrombocytopenic purpura. Blood 2004; 103(12): 4514-9.

38. Luken B M, Turenhout E A, Hulstein J J, et al. The spacer domain of ADAMTS13 contains a major binding site for antibodies in patients with thrombotic thrombocytopenic purpura. Thromb Haemost 2005; 93(2): 267-74.

39. Blackshear J L, Schaff H V, Ommen S R, et al. Hypertrophic obstructive cardiomyopathy, bleeding history, and acquired von Willebrand syndrome: response to septal myectomy. Mayo Clin Proc 2011; 86(3): 219-24.

40. Favaloro E J, Bonar R, Marsden K. Different bleeding risk in type 2A and 2M von Willebrand disease: a 2-year prospective study in 107 patients: a rebuttal. J Thromb Haemost 2012; 10(7): 1455-8.

41. Rolf N, Suttorp M, Budde U, et al. Essential thrombocythaemia in a teenage girl resulting in acquired von Willebrand syndrome with joint haemorrhage and menorrhagia. Thromb Haemost 2010; 103(6): 1272-4.

42. Heilmann C, Geisen U, Beyersdorf F, et al. Acquired von Willebrand syndrome in patients with extracorporeal life support (ECLS). Intensive Care Med 2012; 38(1): 62-8.

The invention claimed is:

1. An isolated monoclonal antibody that specifically binds to a peptide of SEQ ID NO: 1 derived from the D4 domain of human von Willebrand factor (VWF), which competes for binding to VWF D4 domain with A Disintegrin And Metalloprotease with ThrmnboSpondin domains-13 (ADAMTS13) and inhibits between 50 and 80% of ADAMTS13-mediated degradation of high molecular weight (HMW)-multimers of VWF, wherein a heavy chain variable region comprises
   i) an amino acid sequence as set forth in SEQ ID NO:2, or
   ii) an H-CDR1, having an amino acid sequence as set forth in SEQ ID NO:3; an H-CDR2, having an amino acid sequence as set forth in SEQ ID NO:4; and an H-CDR3, having an amino acid sequence as set forth in SEQ ID NO:5;
and
a light chain variable region comprises
   iii) an amino acid sequence as set forth in SEQ ID NO:6, or
   iv) a L-CDR1, having an amino acid sequence as set forth in SEQ ID NO:7; a L-CDR2, having an amino acid sequence as set forth in SEQ ID NO:8; and a L-CDR3, having an amino acid sequence as set forth in SEQ ID NO:9.

2. The antibody according to claim 1, wherein the heavy chain variable region of said antibody has the amino acid sequence as set forth in SEQ ID NO: 2 and the light chain variable region has the amino acid sequence as set forth in SEQ ID NO: 6.

3. The antibody according to claim 1, which is a chimeric antibody.

4. The antibody according to claim 1, which is a humanized antibody.

5. A fragment of a monoclonal antibody that specifically binds to a peptide of SEQ ID NO: 1 derived from the D4 domain of human von Willebrand factor (VWF), competes for binding to VWF D4 domain with A Disintegrin And Metalloprotease with ThromboSpondin domains-13 (ADAMTS13) and inhibits between 50 and 80% of ADAMTS13-mediated degradation of high molecular weight (HMW)-multimers of VWF, wherein the fragment is selected from the group consisting of Fv, Fab, F(ab')2, Fab', dsFv, scFv, sc(Fv)2 and diabodies, wherein the fragment comprises: a heavy chain variable region comprising
   i) an amino acid sequence as set forth in SEQ ID NO:2, or
   ii) an H-CDR1, having an amino acid sequence as set forth in SEQ ID NO:3; an H-CDR2, having an amino acid sequence as set forth in SEQ ID NO:4; and an H-CDR3, having an amino acid sequence as set forth in SEQ IC ID NO:5;
and
a light chain variable region comprising
   iii) an amino acid sequence as set forth in SEQ ID NO:6, or
   iv) a L-CDR1, having an amino acid sequence as set forth in SEQ ID NO:7; a L-CDR2, having an amino acid sequence as set forth in SEQ ID NO:8; and a L-CDR3, having an amino acid sequence as set forth in SEQ ID NO:9.

6. A pharmaceutical composition comprising a monoclonal antibody that specifically binds to a peptide of SEQ ID NO: 1 derived from the D4 domain of human von Willebrand factor (VWF), which competes for binding to VWF D4 domain with A Disintegrin And Metalloprotease with ThromboSpondin domains-13 (ADAMTS13) and inhibits between 50 and 80% of ADAMTS13-mediated degradation of high molecular weight (HMW)-multimers of VWF; or a fragment of the monoclonal antibody, wherein the monoclonal antibody or the fragment of the monoclonal antibody comprises:
a heavy chain variable region comprising
   i) an amino acid sequence as set forth in SEQ ID NO:2, or
   ii) an H-CDR1, having an amino acid sequence as set forth in SEQ ID NO:3; an H-CDR2, having an amino acid sequence as set forth in SEQ ID NO:4; and an H-CDR3, having an amino acid sequence as set forth in SEQ ID NO:5;
and
a light chain variable region comprising
   iii) an amino acid sequence as set forth in SEQ ID NO:6, or
   iv) a L-CDR1, having an amino acid sequence as set forth in SEQ ID NO:7; a L-CDR2, having an amino acid sequence as set forth in SEQ ID NO:8; and a L-CDR3, having an amino acid sequence as set forth in SEQ ID NO:9.

7. The antibody of claim 3, which is a chimeric mouse/human antibody.

8. The pharmaceutical composition of claim 6 wherein the fragment of the monoclonal antibody that specifically binds to the D4 domain of human von Willebrand factor (VWF), competes for binding to VWF D4 domain with A Disintegrin and Metalloprotease with ThromboSpondin domains-13 (ADAMTS13) and inhibits between 50 and 80% of ADAMTS13-mediated degradation of high molecular weight (HMW)-multimers of VWF, wherein the fragment is selected from the group consisting of Fv, Fab, F(ab')2, Fab', dsFv, scFv, sc(Fv)2 and diabodies.

9. The pharmaceutical composition of claim 6 wherein the antibody comprises the heavy chain variable region having the amino acid sequence as set forth in SEQ ID NO: 2 and the light chain variable region having the amino acid sequence as set forth in SEQ ID NO: 6.

10. The pharmaceutical composition of claim 6 wherein the antibody is a chimeric antibody.

11. The pharmaceutical composition of claim 6 wherein the antibody is a humanized antibody.

* * * * *

SEQUENCE LISTING

```
<160> NUMBER OF SEQ ID NOS: 11

<210> SEQ ID NO 1
<211> LENGTH: 12
<212> TYPE: PRT
<213> ORGANISM: Artificial
<220> FEATURE:
<223> OTHER INFORMATION: Synthetic Peptide covering residues 2158-2169
      of VWF
```

<400> SEQUENCE: 1

Thr Phe Tyr Ala Ile Cys Gln Gln Asp Ser Cys His
1               5                   10

<210> SEQ ID NO 2
<211> LENGTH: 455
<212> TYPE: PRT
<213> ORGANISM: Artificial
<220> FEATURE:
<223> OTHER INFORMATION: Synthetic mAb508 VH

<400> SEQUENCE: 2

Met Arg Val Leu Ile Leu Leu Cys Leu Phe Thr Ala Phe Pro Gly Leu
1               5                   10                  15

Leu Ser Asp Val Gln Leu Gln Glu Ser Gly Pro Asp Leu Val Glu Pro
                20                  25                  30

Ser Gln Ser Leu Ser Leu Ser Cys Thr Val Thr Gly Tyr Ser Ile Thr
            35                  40                  45

Ser Gly Tyr Ser Trp His Trp Ile Arg Gln Phe Pro Gly Asn Lys Leu
        50                  55                  60

Glu Trp Leu Gly Tyr Ile His Tyr Ser Gly Thr Thr Thr Tyr Asn Pro
65                  70                  75                  80

Ser Leu His Ser Arg Val Ser Ile Thr Arg Asp Thr Ser Lys Asn Gln
                85                  90                  95

Phe Phe Leu Gln Leu Asn Ser Val Ser Thr Glu Asp Thr Ala Thr Tyr
            100                 105                 110

Phe Cys Gly Arg Glu Gly Tyr His Trp Gly Gln Gly Thr Thr Leu Thr
        115                 120                 125

Val Ser Ser Ala Lys Thr Thr Pro Pro Ser Val Tyr Pro Leu Ala Pro
130                 135                 140

Gly Ser Ala Ala Gln Thr Asn Ser Met Val Thr Leu Gly Cys Leu Val
145                 150                 155                 160

Lys Gly Tyr Phe Pro Glu Pro Val Thr Val Thr Trp Asn Ser Gly Ser
                165                 170                 175

Leu Ser Ser Gly Val His Thr Phe Pro Ala Val Leu Gln Ser Asp Leu
            180                 185                 190

Tyr Thr Leu Ser Ser Ser Val Thr Val Pro Ser Ser Thr Trp Pro Ser
        195                 200                 205

Glu Thr Val Thr Cys Asn Val Ala His Pro Ala Ser Ser Thr Lys Val
    210                 215                 220

Asp Lys Lys Ile Val Pro Arg Asp Cys Gly Cys Lys Pro Cys Ile Cys
225                 230                 235                 240

Thr Val Pro Glu Val Ser Ser Val Phe Ile Phe Pro Pro Lys Pro Lys
                245                 250                 255

Asp Val Leu Thr Ile Thr Leu Thr Pro Lys Val Thr Cys Val Val Val
            260                 265                 270

Asp Ile Ser Lys Asp Asp Pro Glu Val Gln Phe Ser Trp Phe Val Asp
        275                 280                 285

Asp Val Glu Val His Thr Ala Gln Thr Gln Pro Arg Glu Glu Gln Phe
    290                 295                 300

Asn Ser Thr Phe Arg Ser Val Ser Glu Leu Pro Ile Met His Gln Asp
305                 310                 315                 320

Trp Leu Asn Gly Lys Glu Phe Lys Cys Arg Val Asn Ser Ala Ala Phe
                325                 330                 335

Pro Ala Pro Ile Glu Lys Thr Ile Ser Lys Thr Lys Gly Arg Pro Lys

```
                  340                 345                 350
Ala Pro Gln Val Tyr Thr Ile Pro Pro Lys Glu Gln Met Ala Lys
            355                 360                 365

Asp Lys Val Ser Leu Thr Cys Met Ile Thr Asp Phe Phe Pro Glu Asp
    370                 375                 380

Ile Thr Val Glu Trp Gln Trp Asn Gly Gln Pro Ala Glu Asn Tyr Lys
385                 390                 395                 400

Asn Thr Gln Pro Ile Met Asp Thr Asp Gly Ser Tyr Phe Val Tyr Ser
                405                 410                 415

Lys Leu Asn Val Gln Lys Ser Asn Trp Glu Ala Gly Asn Thr Phe Thr
            420                 425                 430

Cys Ser Val Leu His Glu Gly Leu His Asn His His Thr Glu Lys Ser
        435                 440                 445

Leu Ser His Ser Pro Gly Lys
        450                 455

<210> SEQ ID NO 3
<211> LENGTH: 11
<212> TYPE: PRT
<213> ORGANISM: Artificial
<220> FEATURE:
<223> OTHER INFORMATION: Synthetic mAb508 H-CDR1

<400> SEQUENCE: 3

Gly Tyr Ser Ile Thr Ser Gly Tyr Ser Trp His
1               5                   10

<210> SEQ ID NO 4
<211> LENGTH: 16
<212> TYPE: PRT
<213> ORGANISM: Artificial
<220> FEATURE:
<223> OTHER INFORMATION: Synthetic mAb508 H-CDR2

<400> SEQUENCE: 4

Tyr Ile His Tyr Ser Gly Thr Thr Thr Tyr Asn Pro Ser Leu His Ser
1               5                   10                  15

<210> SEQ ID NO 5
<211> LENGTH: 4
<212> TYPE: PRT
<213> ORGANISM: Artificial
<220> FEATURE:
<223> OTHER INFORMATION: Synthetic mAb508 H-CDR3

<400> SEQUENCE: 5

Glu Gly Tyr His
1

<210> SEQ ID NO 6
<211> LENGTH: 238
<212> TYPE: PRT
<213> ORGANISM: Artificial
<220> FEATURE:
<223> OTHER INFORMATION: Synthetic mAb 508 VL

<400> SEQUENCE: 6

Met Lys Leu Pro Val Arg Leu Leu Val Leu Met Phe Trp Ile Pro Gly
1               5                   10                  15

Ser Thr Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
```

```
                  35                  40                  45
Val His Ser Ile Gly Asn Thr Tyr Leu His Trp Tyr Leu Gln Lys Pro
 50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                     85                  90                  95

Leu Lys Ile Ser Arg Val Glu Ala Glu Asp Leu Gly Val Tyr Phe Cys
                    100                 105                 110

Ser Gln Thr Thr His Val Pro Leu Thr Phe Gly Gly Gly Thr Arg Leu
                    115                 120                 125

Glu Ile Lys Arg Ala Asp Ala Ala Pro Thr Val Ser Ile Phe Pro Pro
                    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                    165                 170                 175

Ser Glu Arg Gln Asn Gly Val Leu Asn Ser Trp Thr Asp Gln Asp Ser
                    180                 185                 190

Lys Asp Ser Thr Tyr Ser Met Ser Ser Thr Leu Thr Leu Thr Lys Asp
                    195                 200                 205

Glu Tyr Glu Arg His Asn Ser Tyr Thr Cys Glu Ala Thr His Lys Thr
                    210                 215                 220

Ser Thr Ser Pro Ile Val Lys Ser Phe Asn Arg Asn Glu Cys
225                 230                 235

<210> SEQ ID NO 7
<211> LENGTH: 16
<212> TYPE: PRT
<213> ORGANISM: Artificial
<220> FEATURE:
<223> OTHER INFORMATION: Synthetic mAb508 L-CDR1

<400> SEQUENCE: 7

Arg Ser Ser Gln Ser Leu Val His Ser Ile Gly Asn Thr Tyr Leu His
1               5                  10                  15

<210> SEQ ID NO 8
<211> LENGTH: 7
<212> TYPE: PRT
<213> ORGANISM: Artificial
<220> FEATURE:
<223> OTHER INFORMATION: Synthetic mAb L-CDR2

<400> SEQUENCE: 8

Lys Val Ser Asn Arg Phe Ser
1               5

<210> SEQ ID NO 9
<211> LENGTH: 9
<212> TYPE: PRT
<213> ORGANISM: Artificial
<220> FEATURE:
<223> OTHER INFORMATION: Synthetic mAb508 L-CDR3

<400> SEQUENCE: 9

Ser Gln Thr Thr His Val Pro Leu Thr
1               5

<210> SEQ ID NO 10
```

<211> LENGTH: 1368
<212> TYPE: DNA
<213> ORGANISM: Artificial
<220> FEATURE:
<223> OTHER INFORMATION: Synthetic mAb508 VH

<400> SEQUENCE: 10

| | |
|---|---|
| atgagagtgc tgattctctt gtgcctgttc acagcctttc ctggtctcct gtctgatgtg | 60 |
| cagcttcagg agtcaggacc tgacctggtg gaaccttctc agtcactttc actctcctgc | 120 |
| actgtcactg gctactccat caccagtggt tatagctggc actggattcg gcagtttcca | 180 |
| ggaaacaaac tggaatggct gggctacatt cactacagtg gcaccactac ctacaaccca | 240 |
| tctctccaca gtcgagtctc tatcactcga gacacgtcca agaaccagtt cttcctgcag | 300 |
| ttgaattctg tgtctactga ggacacggcc acatatttct gtggaagaga aggttaccat | 360 |
| tggggccaag gcaccactct cacagtctcc tcagccaaaa cgacaccccc atctgtctat | 420 |
| ccactggccc ctggatctgc tgcccaaact aactccatgg tgaccctggg atgcctggtc | 480 |
| aagggctatt ccctgagcc agtgacatg acctggaact ctggatccct gtccagcggt | 540 |
| gtgcacacct tcccagctgt cctgcagtct gacctctaca ctctgagcag ctcagtgact | 600 |
| gtcccctcca gcacctggcc cagcgagacc gtcacctgca cgttgccca ccggccagc | 660 |
| agcaccaagg tggacaagaa aattgtgccc agggattgtg gttgtaagcc ttgcatatgt | 720 |
| acagtcccag aagtatcatc tgtcttcatc ttccccccaa agcccaagga tgtgctcacc | 780 |
| attactctga ctcctaaggt cacgtgtgtt gtggtagaca tcagcaagga tgatcccgag | 840 |
| gtccagttca gctggtttgt agatgatgtg gaggtgcaca gctcagac gcaaccccgg | 900 |
| gaggagcagt tcaacagcac tttccgctca gtcagtgaac ttcccatcat gcaccaggac | 960 |
| tggctcaatg gcaaggagtt caatgcagg gtcaacagtg cagctttccc tgcccccatc | 1020 |
| gagaaaacca tctccaaaac caaaggcaga ccgaaggctc acaggtgta caccattcca | 1080 |
| cctcccaagg agcagatggc caaggataaa gtcagtctga cctgcatgat aacagacttc | 1140 |
| ttccctgaag acattactgt ggagtggcag tggaatgggc agccagcgga gaactacaag | 1200 |
| aacactcagc ccatcatgga cacagatggc tcttacttcg tctacagcaa gctcaatgtg | 1260 |
| cagaagagca ctgggaggc aggaaatact ttcacctgct ctgtgttaca tgagggcctg | 1320 |
| cacaaccacc atactgagaa gagcctctcc cactctcctg gtaaatga | 1368 |

<210> SEQ ID NO 11
<211> LENGTH: 717
<212> TYPE: DNA
<213> ORGANISM: Artificial
<220> FEATURE:
<223> OTHER INFORMATION: Synthetic mAb508 VL

<400> SEQUENCE: 11

| | |
|---|---|
| atgaagttgc tgttaggct gttggtgctg atgttctgga ttcctggttc caccagtgat | 60 |
| gttgtgatga cccaaactcc actctccctg cctgtcagtc ttggagatca agcctccatc | 120 |
| tcttgcagat ctagtcagag tcttgtacac agcattggaa acacctattt acattggtac | 180 |
| ctgcagaagc caggccagtc tccaaaactc ctgatctaca agtctccaa tcgattttct | 240 |
| ggggtcccag acagattcag tggcagtgga tcagggacag atttcacact caagatcagc | 300 |
| agagtggagg ctgaggatct gggagtttat ttctgctctc aaactacaca tgttcctctg | 360 |
| acgttcggtg gaggcaccag gttggaaatc aaacggctg atgctgcacc aactgtatcc | 420 |
| atcttcccac catccagtga gcagttaaca tctggaggtg cctcagtcgt gtgcttcttg | 480 |

```
aacaacttct accccaaaga catcaatgtc aagtggaaga ttgatggcag tgaacgacaa      540
aatggcgtcc tgaacagttg gactgatcag gacagcaaag acagcaccta cagcatgagc      600
agcaccctca cgttgaccaa ggacgagtat gaacgacata acagctatac ctgtgaggcc      660
actcacaaga catcaacttc acccattgtc aagagcttca acaggaatga gtgttag        717
```